United States Patent
Nishino et al.

(10) Patent No.: US 8,149,116 B2
(45) Date of Patent: Apr. 3, 2012

(54) PORTABLE RADIOGRAPHIC IMAGE CONVERSION DEVICE, WARNING DEVICE AND COMPUTER-READABLE RECORDING MEDIUM

(75) Inventors: Naoyuki Nishino, Kanagawa (JP); Yasunori Ohta, Kanagawa (JP); Keiji Tsubota, Kanagawa (JP); Yutaka Yoshida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 475 days.

(21) Appl. No.: 12/503,089

(22) Filed: Jul. 15, 2009

(65) Prior Publication Data

US 2010/0019900 A1 Jan. 28, 2010

(30) Foreign Application Priority Data

Jul. 22, 2008 (JP) .................................. 2008-188565
Jul. 22, 2008 (JP) .................................. 2008-188603

(51) Int. Cl.
*G08B 21/00* (2006.01)

(52) U.S. Cl. ........ 340/540; 340/687; 340/3.3; 340/3.43; 250/582; 714/799

(58) Field of Classification Search .................. 340/540, 340/687, 686.2, 3.1, 3.3, 3.43, 5.1; 250/370.08, 250/370.09, 393, 354.1, 580, 582; 714/799, 714/E11.031, E11.001; 378/116, 117, 62, 378/98.8, 189; 398/130

See application file for complete search history.

(56) References Cited

U.S. PATENT DOCUMENTS

| | | | | |
|---|---|---|---|---|
| 6,855,936 B2 * | 2/2005 | Yamamoto | ............... | 250/370.09 |
| 7,528,376 B2 * | 5/2009 | Shoji | ........................ | 250/370.09 |
| 2009/0214220 A1 * | 8/2009 | Nishino et al. | ................ | 398/130 |
| 2011/0049370 A1 * | 3/2011 | Yoshida et al. | ............ | 250/354.1 |
| 2011/0108732 A1 * | 5/2011 | Watanabe | ................ | 250/370.08 |

FOREIGN PATENT DOCUMENTS

JP 2007-44068 A 2/2007

* cited by examiner

*Primary Examiner* — Toan N Pham

(74) *Attorney, Agent, or Firm* — Solaris Intellectual Property Group, PLLC

(57) ABSTRACT

A determination unit of a portable radiographic image conversion device determines, when image information has been generated by an electronic circuit, whether or not a state of connection between a connection terminal and a communication cable is abnormal. Then, when it has been determined by the determination unit that the state of connection is not abnormal, a control unit causes the image information that has been generated to be transmitted by a communication unit, and, when it has been determined by the determination unit that the state of connection is abnormal, the control unit causes the image information that has been generated to be stored in a memory.

13 Claims, 20 Drawing Sheets

PORTABLE RADIOGRAPHIC IMAGE CONVERSION DEVICE, WARNING DEVICE AND COMPUTER-READABLE RECORDING MEDIUM

CROSS-REFERENCE TO RELATED APPLICATIONS

This application is based on and claims priority under 35 USC 119 from Japanese Patent Application No. 2008-188565 filed Jul. 22, 2008 and Japanese Patent Application No. 2008-188603 filed Jul. 22, 2008.

BACKGROUND

1. Technical Field

This invention relates to a portable radiographic image conversion device, a warning device and a computer-readable recording medium.

2. Related Art

In recent years, flat panel detectors (FPD) that comprise a radiation sensitive layer disposed on a thin-film transistor (TFT) active matrix substrate and can directly convert radiation into digital data have been put to practical use, and portable radiographic image capturing devices (called "electronic cassettes" below) that use an FPD or the like to generate image information representing a radiographic image expressed by radiation with which the electronic cassette has been irradiated and store the generated image information have been put to practical use.

Electronic cassettes are portable, so they can also capture images of patients lying on a stretcher or a bed as they are, and electronic cassettes can flexibly accommodate patients who cannot move, because the area of the patient of which an image is to be captured can be adjusted by changing the position of the electronic cassette.

It has been common for an electronic cassette to be connected via a communication cable to a control terminal (a so-called console) because of power supply or data transfer limitations. For this reason, a connection terminal for attaching and detaching the communication cable is disposed in the electronic cassette. The connection terminal of the electronic cassette is connected to the communication cable when a radiographic image is to be captured, and the electronic cassette transmits the image information that has been generated by image capture to the console via the communication cable.

Incidentally, when the communication cable is configured to be attachable and detachable, unplugging of the cable becomes a problem. In particular, it is easy for unplugging of the cable to occur because the electronic cassette is moved in order to adjust the image capture position at the time of image capture in a state where the communication cable is connected to the connection terminal of the electronic cassette.

As a technology that addresses unplugging of the cable, there has been disclosed a technology that prohibits image capture when the communication cable is unplugged (see Japanese Patent Application Laid-Open Publication (JP-A) No. 2007-44068).

Incidentally, when the communication cable is configured to be attachable and detachable, there are cases where, once the cable is unplugged, the state of connection between the connection terminal and the communication cable becomes insecure and it becomes easier for unplugging of the cable to occur. In such cases, there has been the problem that, with the technology that prohibits image capture when the communication cable is unplugged, image capture ends up being prohibited by unplugging of the cable, and a radiographic image cannot be smoothly captured.

SUMMARY

The present invention has been made in view of the above circumstances and provides a portable radiographic image conversion device, a warning device and a computer-readable recording medium.

The present invention provides a portable radiographic image conversion device comprising: an electronic circuit that generates image information representing a radiographic image corresponding to an amount of radiation with which the electronic circuit has been irradiated from an external unit; a connection terminal for connecting a communication cable that is connected to an external device; a communication unit that performs communication with the external device via the communication cable; a memory for storing the image information; a determination unit which, when the image information has been generated by the electronic circuit, determines whether or not a state of connection between the connection terminal and the communication cable is abnormal; and a control unit which, when it has been determined by the determination unit that the state of connection is not abnormal, causes the image information that has been generated to be transmitted by the communication unit and, when it has been determined by the determination unit that the state of connection is abnormal, causes the image information that has been generated to be stored in the memory.

According to the portable radiographic image conversion device pertaining to the present invention, the determination unit determines, when the image information has been generated by the electronic circuit, whether or not the state of connection between the connection terminal and the communication cable is abnormal. Additionally, when it has been determined by the determination unit that the state of connection is not abnormal, the control unit causes the image information that has been generated to be transmitted by the communication unit, and, when it has been determined by the determination unit that the state of connection is abnormal, the control unit causes the image information that has been generated to be stored in the memory.

In this manner, when the state of connection between the connection terminal and the communication cable is abnormal, a radiographic image can be smoothly captured, without interrupting image capture, by causing the image information representing a radiographic image that has been generated to be stored in the memory.

The portable radiographic image conversion device pertaining to the present invention may further comprise a communication quality detection unit that detects quality of communication via the communication cable, so that the determination unit can determine whether or not the state of connection between the connection terminal and the communication cable is abnormal on the basis of the communication quality that has been detected by the communication quality detection unit.

The portable radiographic image conversion device pertaining to the present invention may further comprise a mechanical switch that is installed in a position where the communication cable is disposed when the communication cable and the connection terminal are connected to each other, so that the determination unit can determine whether or not the state of connection between the connection terminal and the communication cable is abnormal on the basis of an ON or OFF state of the mechanical switch.

The portable radiographic image conversion device pertaining to the present invention may further comprise a sensor that detects whether or not the communication cable is connected to the connection terminal, so that the determination unit can determine whether or not the state of connection between the connection terminal and the communication cable is abnormal on the basis of the detection result of the sensor.

The portable radiographic image conversion device pertaining to the present invention may further comprise a holding member for holding the communication cable connected to the connection terminal and a sensor that detects a state of holding of the communication cable by the holding member, so that the determination unit can determine whether or not the state of connection between the connection terminal and the communication cable is abnormal on the basis of the detection result of the sensor.

The determination unit pertaining to the present invention can determine whether or not the state of connection between the connection terminal and the communication cable is abnormal by determining whether or not a predetermined signal has been received by the communication unit.

The memory can be configured by a volatile memory or a nonvolatile memory.

The present invention also provides a warning device comprising: an acquisition unit which, with respect to a radiographic image capturing device equipped with a connection terminal and a generation unit that generates image information representing a radiographic image expressed by radiation with which the generation unit has been irradiated, and which radiographic image capturing device transmits, via a communication cable connected to the connection terminal, the image information that has been generated, acquires state information representing a state of connection between the connection terminal and the communication cable; a determination unit that determines whether or not the communication cable connected to the connection terminal is inappropriate for transmission of the image information on the basis of the state information that has been acquired by the acquisition unit; and a control unit that controls a warning unit such that a warning is issued when it has been determined by the determination unit that the communication cable connected to the connection terminal is inappropriate for transmission of the image information.

According to the warning device pertaining to the present invention, the acquisition unit acquires, with respect to the radiographic image capturing device equipped with the connection terminal and the generation unit that generates image information representing a radiographic image expressed by radiation with which the generation unit has been irradiated, and which radiographic image capturing device transmits, via the communication cable connected to the connection terminal, the image information that has been generated, the state information representing the state of connection between the connection terminal and the communication cable, the determination unit determines whether or not the communication cable connected to the connection terminal is inappropriate for transmission of the image information on the basis of the state information that has been acquired by the acquisition unit, and the control unit controls the warning unit such that a warning is issued when it has been determined by the determination unit that the communication cable connected to the connection terminal is inappropriate for transmission of the image information.

In this manner, according to the warning device of the present invention, the acquisition unit acquires the state information representing the past state of communication between the connection terminal of the radiographic image capturing device and the communication cable, the determination unit determines whether or not the communication cable connected to the connection terminal is inappropriate for transmission of the image information on the basis of the state information that has been acquired, and the control unit controls the warning unit such that a warning is issued when it has been determined that the communication cable connected to the connection terminal is inappropriate for transmission of the image information, so by replacing the communication cable in accordance with the warning, the state of communication between the connection terminal and the communication cable becomes secure and it becomes possible to securely transfer the image information, so a radiographic image can be smoothly captured.

The warning device of the present invention may be configured such that the determination unit determines whether or not the communication cable is inappropriate for transmission of the image information by determining whether or not the state of connection represented by the state information satisfies a condition determined beforehand as being inappropriate for the transmission of image information.

Thus, whether or not the communication cable is inappropriate for the transmission of image information can be appropriately determined.

Further, it is preferable for the warning device of the present invention to be configured such that the determination unit performs the determination at a predetermined timing in a preparatory stage of capturing a radiographic image.

Thus, the determination unit performs the determination at a predetermined timing in a preparatory stage of image capture and the warning unit issues a warning when the communication cable is inappropriate for transmission of the image information, whereby a situation where the state of connection between the connection terminal and the communication cable becomes insecure at the time of capturing a radiographic image can be prevented.

Further, in the warning device of the present invention, the state information may be at least one of information representing a physical state of connection between the connection terminal and the communication cable that has been detected by a mechanical switch or a sensor, information representing quality of communication when the communication cable has been connected to the connection terminal and data have been transmitted, and information representing a state of holding of the communication cable when the communication cable is connected to the connection terminal and the communication cable is held in a holding member disposed in the radiographic image capturing device.

According to the portable radiographic image conversion device and the computer-readable recording medium pertaining to the present invention, there is obtained the effect that, when the state of connection between the connection terminal and the communication cable is abnormal, a radiographic image can be smoothly captured, without interrupting image capture, by causing the image information representing a radiographic image that has been generated to be stored in the memory.

According to the warning device and the computer-readable recording medium pertaining to the present invention, the acquisition unit acquires the state information representing the state of communication between the connection terminal of the radiographic image capturing device and the communication cable, the determination unit determines whether or not the communication cable connected to the connection terminal is inappropriate for transmission of the image information on the basis of the state information that has been acquired, and the control unit controls the warning unit such that a warning is issued when it has been determined that the communication cable connected to the connection terminal is inappropriate for transmission of the image information, so there is the effect that a radiographic image can be smoothly captured.

BRIEF DESCRIPTION OF THE DRAWINGS

Exemplary embodiments of the present invention will be described in detail based on the following figures, wherein.

DETAILED DESCRIPTION

Below, the best modes for implementing the present invention will be described in detail with reference to the drawings.

Figure 1:
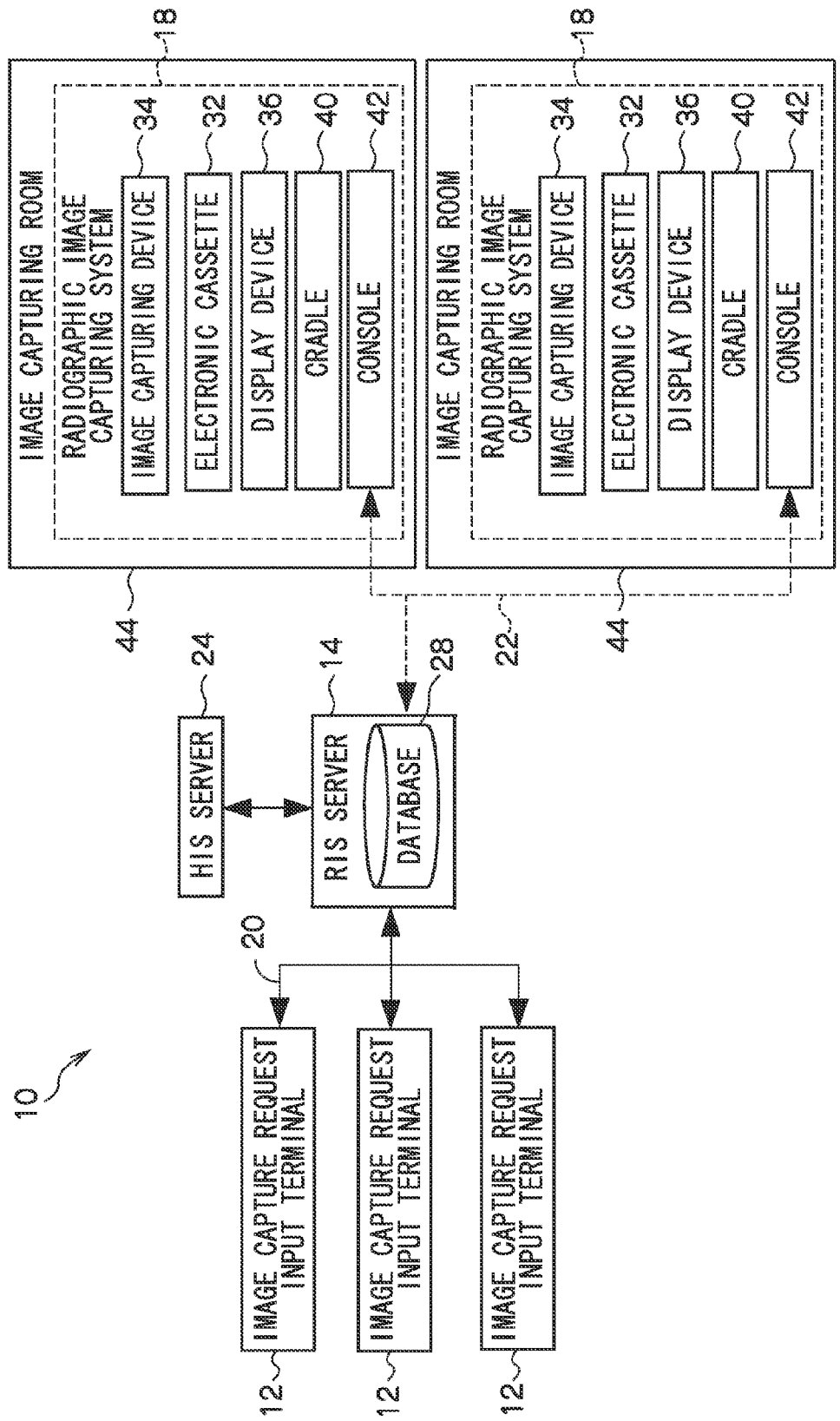
FIG. 1 is a block diagram showing the configuration of a radiology information system pertaining to a first exemplary embodiment of the invention.

First, the configuration of a radiology information system (RIS) 10 (also called "RIS 10" below) pertaining to a first exemplary embodiment will be described. In FIG. 1, there is shown a block diagram showing each component of the RIS 10 pertaining to the first exemplary embodiment.

The RIS 10 is a system for managing information such as medical service appointments and diagnostic records in a radiology department and configures part of a hospital information system (HIS).

The RIS 10 is configured to include plural image capture request input terminals 12 (also called "input terminals 12" below), an RIS server 14, and plural radiographic image capturing systems 18 (also called "image capturing systems 18" below).

The RIS server 14 manages the entire RIS 10 and is configured such that each of the input terminals 12 and the image capturing systems 18 are capable of communicating with each other by a local area network (LAN) cable 20 or a wireless LAN 22. Further, the RIS server 14 is connected to an HIS server 24 that manages the entire HIS.

The input terminals 12 are terminals for doctors 26 (see FIG. 2) or a radiologic technologist to input/browse diagnostic information and facility reservations. A request to capture a radiographic image (image capture reservation) is performed from the input terminals 12. Each of the input terminals 12 is configured by a personal computer equipped with a display device, and the input terminals 12 are connected by the LAN to the RIS server 14 and are capable of communicating with each other.

The RIS server 14 receives the image capture requests from the input terminals 12 and manages radiographic image capture schedules in the image capturing systems 18. The RIS server 14 is configured to include a database 28.

The database 28 is configured to include information relating to a patient 30 (see FIG. 2), such as attribute information (name, sex, date of birth, age, blood type, patient ID, etc.) of the patient 30, medical history, consultation history, radiographic images captured in the past, etc., and information relating to electronic cassettes 32 of the capturing systems 18, such as ID numbers, types, sizes, sensitivities, useable image capture sites (content of image capture requests the electronic cassettes 12 are capable of accommodating), starting dates of use, numbers of times used, etc.

The image capturing systems 18 capture radiographic images by operation of the doctors 26 or a radiologic technologist in response to an instruction from the RIS server 14. Each of the capturing systems 18 is equipped with an image capturing device 34 that irradiates a subject with radiation X comprising a radiation amount corresponding to image capture conditions, an electronic cassette 32 that includes a built-in radiation detector 60 (see FIG. 3) that detects the radiation X that has been transmitted through the patient 30 and converts that radiation X into radiographic image information, a display device 36 that displays a radiographic image based on the radiation X that has been detected by the radiation detector 60, a cradle 40 that charges a battery built into the electronic cassette 32, and a console 42 that controls the electronic cassette 32, the image capturing device 34, the display device 36 and the cradle 40.

Figure 2:
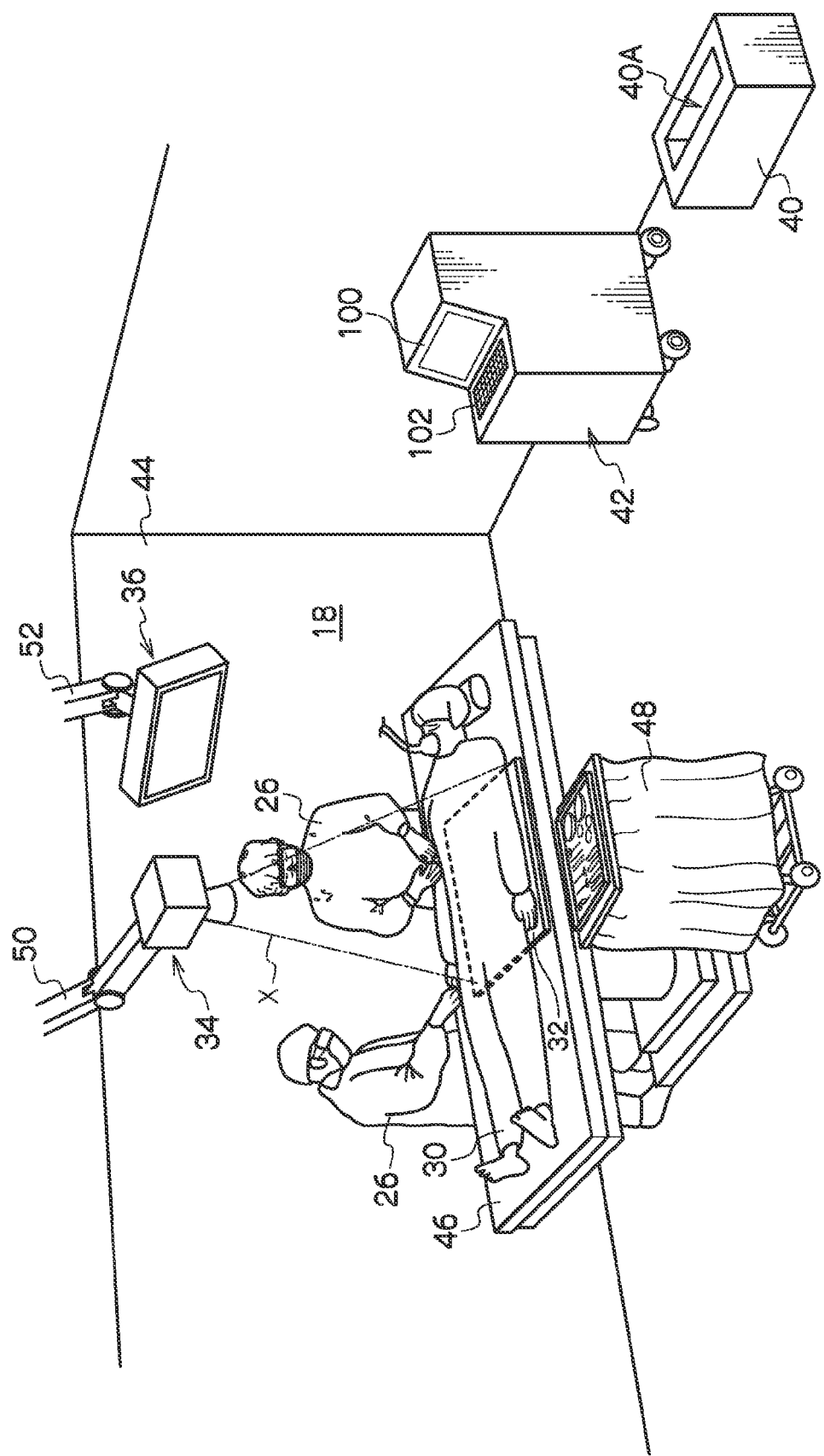
FIG. 2 is a diagram showing an operating room in which a radiographic image capturing system pertaining to the first exemplary embodiment of the invention is disposed.

In FIG. 2, there is shown the inside of an operating room 44 that serves as an image capturing room in which one of the capturing systems 18 is installed as one example where the image capturing system 18 pertaining to the present exemplary embodiment is disposed. In the image capturing system 18 pertaining to the present exemplary embodiment, the console 42 is connected to each of the electronic cassette 32, the image capturing device 34 and the display device 36 by cables, and the devices transmit and receive various information by wired communication. In FIG. 2, the cables that interconnect the devices are omitted.

In the operating room 44 of FIG. 2, in addition to the image capturing system 18, an operating table 46 on which the patient 30 lies is disposed, and an instrument table 48 on which are placed various instruments that the doctors 26 use in surgery is disposed on the side of the operating table 46. Further, various devices needed for surgery, such as an anesthesia machine, an evacuator, an electrocardiograph and a blood pressure monitor, are disposed around the operating table 46 (these devices are omitted in FIG. 2).

The image capturing device 34 is coupled to an adjustable arm 50. The image capturing device 34 is capable of being moved to a desired position corresponding to the area of the patient 30 of which an image is to be captured, and the image capturing device 34 is capable of being withdrawn to a position where it does not hinder surgery by the doctors 26. Similarly, the display device 36 is coupled to an adjustable arm 52. The display device 36 is capable of being moved to a position where the doctors 26 can easily check the radiographic image that has been captured.

In the cradle 40, there is formed a housing portion 40A that is capable of housing the electronic cassette 32.

When the electronic cassette 32 stands by, the electronic cassette 32 is housed in the housing portion 40A of the cradle 40, and the built-in battery is charged. At the time when a radiographic image is to be captured, the electronic cassette 32 is removed from the cradle 40, a communication cable is connected to the electronic cassette 32, and the electronic cassette 32 is disposed in the area of the patient 30 of which an image is to be captured.

It will be noted that the electronic cassette 32 is not limited to being used in the operating room 44 and can also be applied to medical screenings and rounds inside a hospital, for example.

Figure 3:
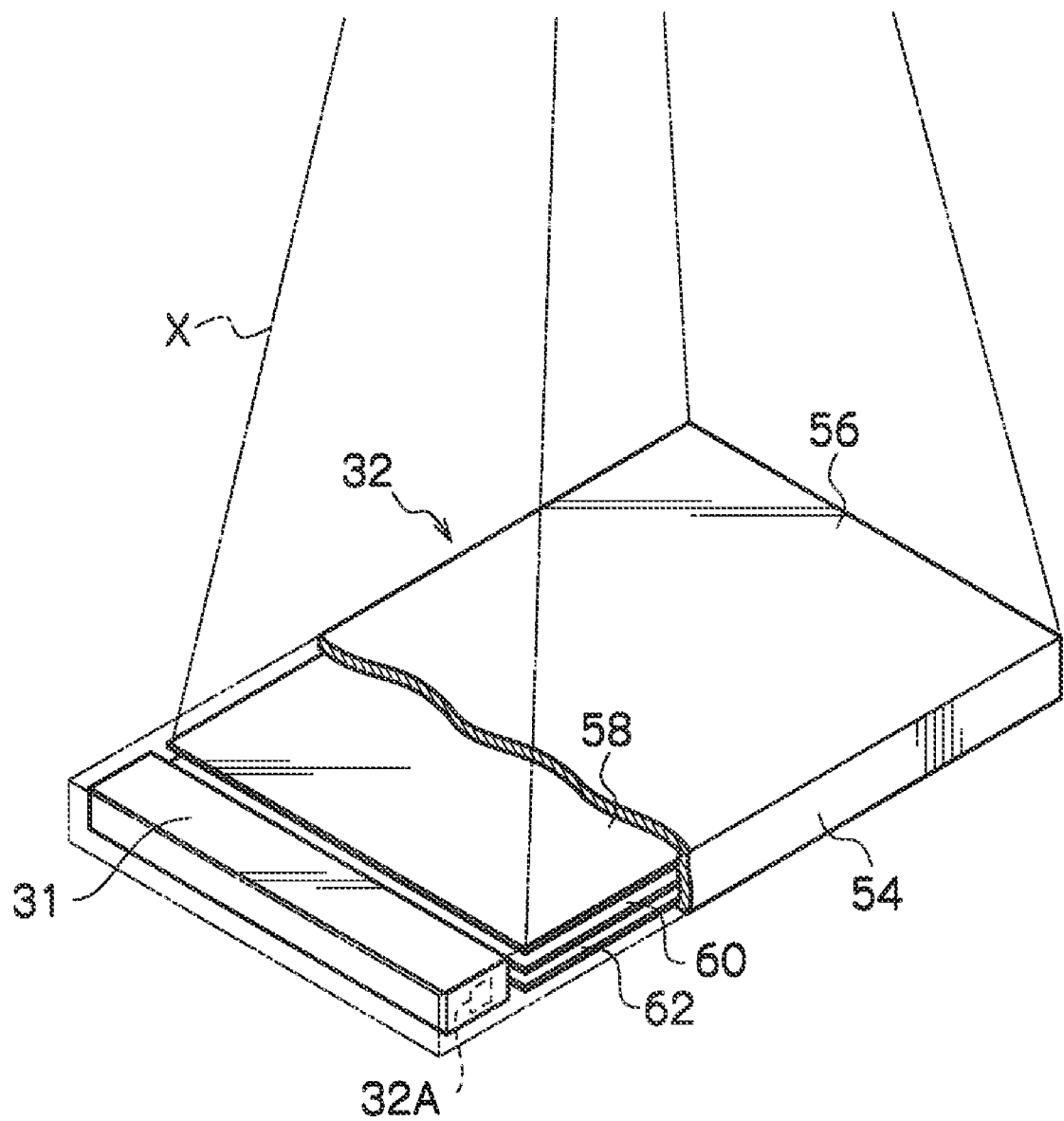
FIG. 3 is a perspective diagram showing the internal configuration of an electronic cassette pertaining to the first exemplary embodiment of the invention.

In FIG. 3, there is shown the internal configuration of the electronic cassette 32 pertaining to the first exemplary embodiment. The electronic cassette 32 is equipped with a casing 54 that comprises a material that allows the radiation X to be transmitted therethrough, and the electronic cassette 32 is configured to have a waterproof and hermetic structure.

There is the fear that blood or another contaminant may adhere to the electronic cassette 32 when the electronic cassette 32 is used in the operating room 44 or the like. Thus, the electronic cassette 32 is configured to have a waterproof and hermetic structure and is washed with an antiseptic as needed, whereby the one electronic cassette 32 can be used repeatedly. A connection terminal 32A for connecting a communication cable is disposed in a side surface of the casing 54. Inside the casing 54, there are disposed, in order from an irradiated surface 56 side of the casing 54 that is irradiated with the radiation X, a grid 58 that removes scattered radiation of the radiation X resulting from the patient 30, a radiation detector 60 that detects the radiation X that has been transmitted through the patient 30, and a lead plate 62 that absorbs back scattered radiation of the radiation X. It will be noted that the irradiated surface 56 of the casing 54 may also be configured by the grid 58.

Further, a case 31 that houses various circuits including a microcomputer and a rechargeable secondary battery are disposed on one end side of the inside of the casing 54. The radiation detector 60 and the various circuits are actuated by power supplied from the secondary battery disposed in the case 31. It is desirable for a lead plate or the like to be disposed on the irradiated surface 56 side of the case 31 in order to avoid a situation where the various circuits housed inside the case 31 sustain damage in accompaniment with being irradiated with the radiation X.

Figure 4:
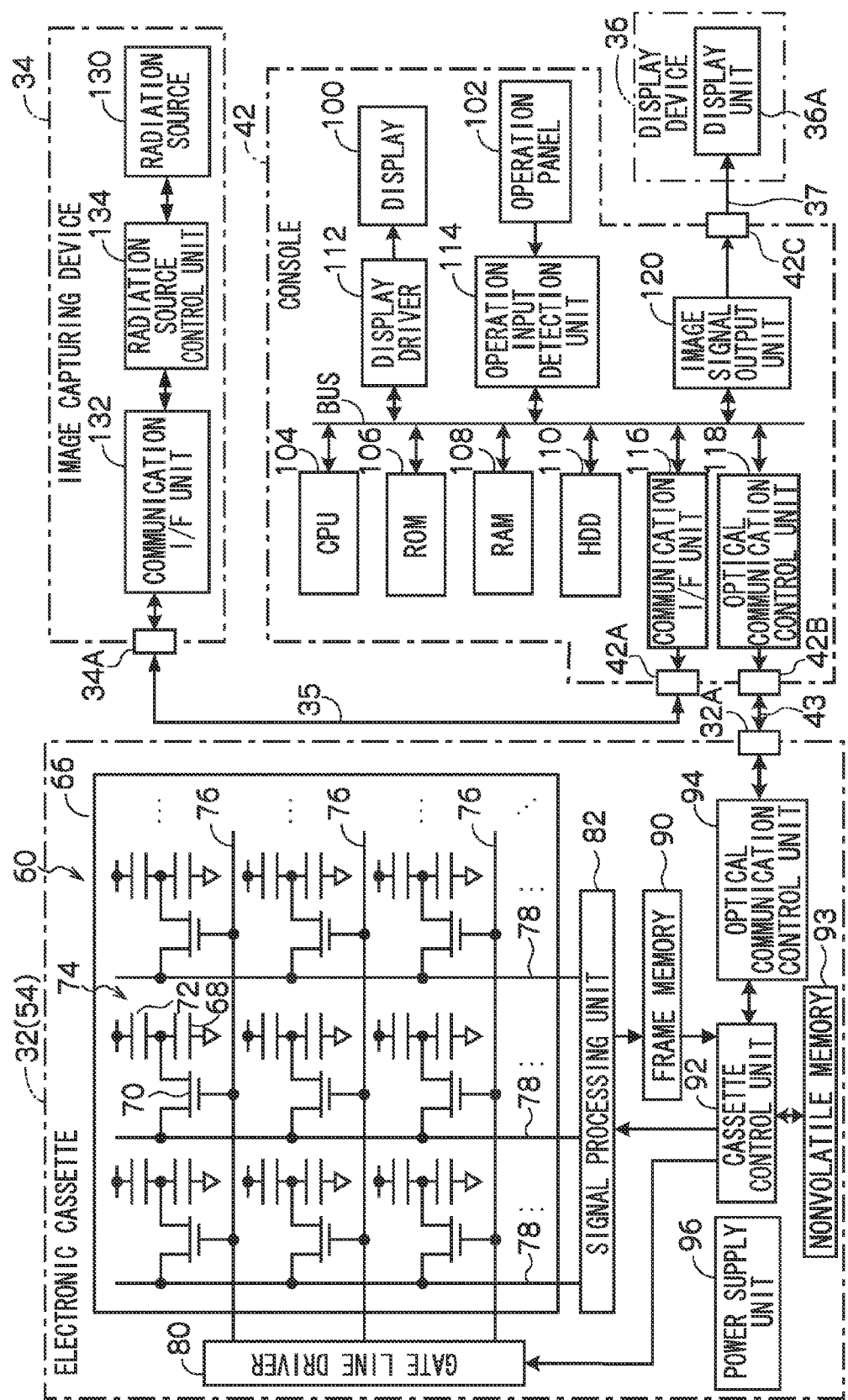
FIG. 4 is a block diagram showing the detailed configuration of the radiographic image capturing system pertaining to the first exemplary embodiment of the invention.

In FIG. 4, there is shown a block diagram showing the detailed configuration of the radiographic image capturing system 18 pertaining to the present exemplary embodiment.

A connection terminal 34A for performing communication with the console 42 is disposed in the image capturing device 34. A connection terminal 42A for performing communication with the image capturing device 34, a connection terminal 42B for performing communication with the electronic cassette 32 and a connection terminal 42C for outputting image signals to the display device 36 are disposed in the console 42.

The image capturing device 34 is connected to the console 42 via a communication cable 35, and the display device 36 is connected to the console 42 via a display cable 37. At the time of capture of a radiographic image, a communication cable 43 is connected to the connection terminal 32A of the electronic cassette 32, and the electronic cassette 32 is connected to the console 42 via the communication cable 43. It will be noted that, in the present exemplary embodiment, an optical communication cable using optical fiber is used for the communication cable 43 in order to perform data transfer between the electronic cassette 32 and the console 42 at a high speed. The transfer of data is performed between the electronic cassette 32 and the console 42 by optical communication.

The radiation detector 60 built into the electronic cassette 32 is configured as a result of a photoelectric conversion layer that absorbs and converts the radiation X into electric charges being layered on a TFT active matrix substrate 66. The photoelectric conversion layer comprises, for example, non-crystalline amorphous selenium (a-Se) whose main component (e.g., having a content percentage equal to or greater than 50%) is selenium. When the photoelectric conversion layer is irradiated with the radiation X, the photoelectric conversion layer converts the radiation X with which it has been irradiated into electric charges by generating, inside itself, electric charges (electron-hole pairs) of an electric charge amount corresponding to the amount of the radiation X with which it has been irradiated. It will be noted that the radiation detector 60 may also, instead of a material that directly converts the radiation X into electric charges such as amorphous selenium, use a phosphor material and a photoelectric conversion element (photodiode) to indirectly convert the radiation X into electric charges. As the phosphor material, gadolinium oxysulfide (GOS) and cesium iodide (CsI) are well known. In this case, conversion of the radiation X into light is performed by the phosphor material, and conversion of the light into electric charges is performed by the photodiode of the photoelectric conversion element.

Further, on the TFT active matrix substrate 66, numerous pixel components 74 (in FIG. 4, the photoelectric conversion layer corresponding to the individual pixel components 74 is schematically shown as photoelectric conversion components 72) equipped with storage capacitors 68 that store the electric charges that have been generated by the photoelectric conversion layer and TFTs 70 for reading the electric charges that have been stored in the storage capacitors 68 are disposed in a matrix. The electric charges that have been generated by the photoelectric conversion layer in accompaniment with the irradiation of the electronic cassette 32 with the radiation X are stored in the storage capacitors 68 of the individual pixel components 74. Thus, the image information that had been carried in the radiation X with which the electronic cassette 32 was irradiated is converted into electric charge information and is held in the radiation detector 60.

Further, on the TFT active matrix substrate 66, there are disposed plural gate lines 76, which extend in a constant direction (row direction) and are for switching ON and OFF the TFTs 70 of the individual pixel components 74, and plural data lines 78, which extend in a direction (column direction) orthogonal to the gate lines 76 and are for reading the stored electric charges from the storage capacitors 68 via the TFTs 70 that have been switched ON. The individual gate lines 76 are connected to a gate line driver 80. The individual data lines 78 are attached to a signal processing unit 82. When the electric charges are stored in the storage capacitors 68 of the individual pixel components 74, the TFTs 70 of the individual pixel components 74 are switched ON in order in row units by signals that are supplied via the gate lines 76 from the gate line driver 80. The electric charges that are stored in the storage capacitors 68 of the pixel components 74 whose TFTs 70 have been switched ON are transmitted through the data lines 78 as electric charge signals and are inputted to the signal processing unit 82. Consequently, the electric charges that are stored in the storage capacitors 68 of the individual pixel components 74 are read in order in row units.

Figure 5:
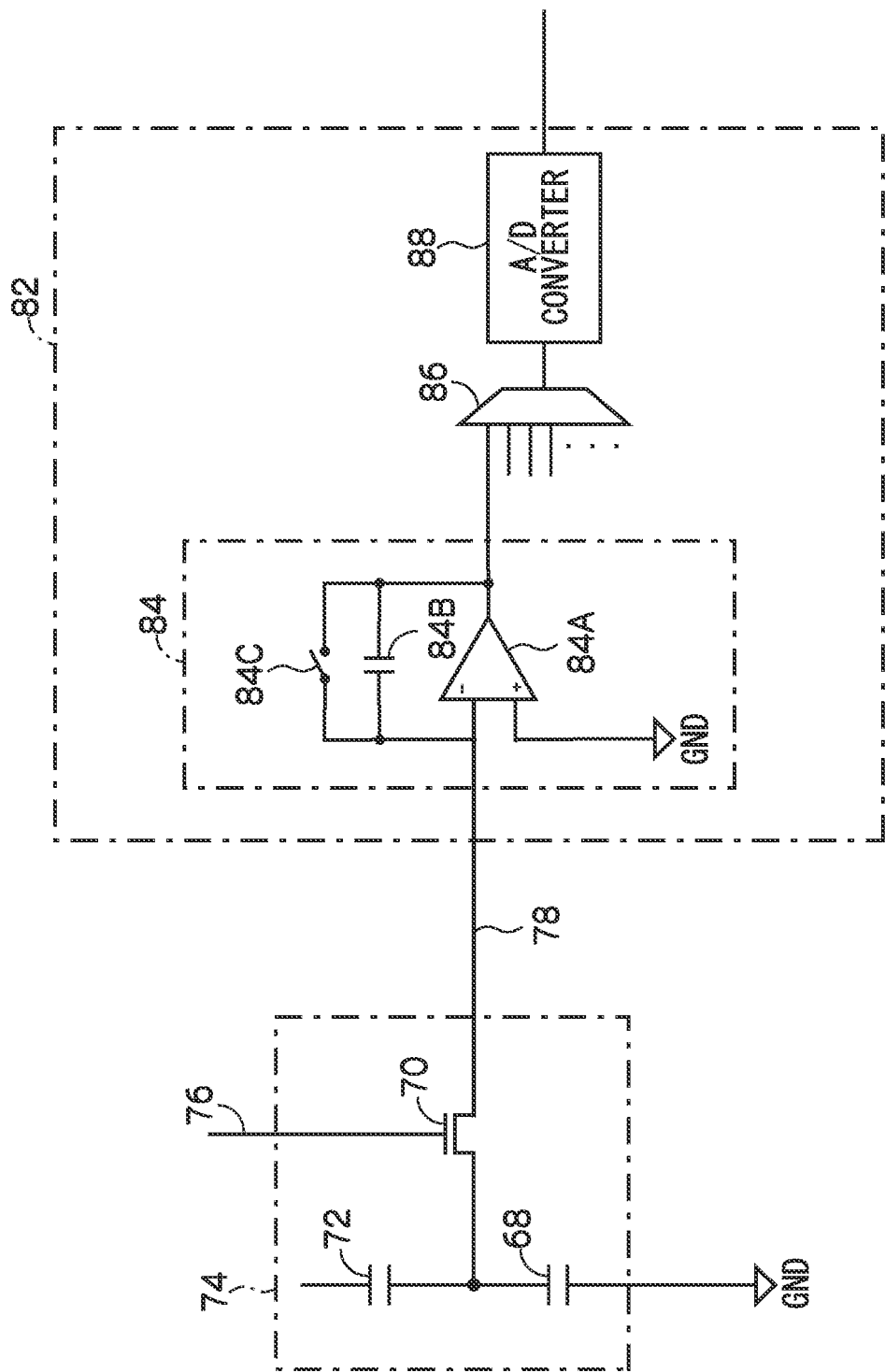
FIG. 5 is an equivalent circuit diagram focusing on one pixel portion of a radiation detector pertaining to the first exemplary embodiment of the invention.

In FIG. 5, there is shown an equivalent circuit diagram focusing on one pixel portion of the radiation detector 60 pertaining to the present exemplary embodiment.

As shown in FIG. 5, a source of the TFT 70 is connected to the data line 78. The data line 78 is connected to the signal processing unit 82. Further, a drain of the TFT 70 is connected to the storage capacitor 68 and to the photoelectric conversion component 72. A gate of the TFT 70 is connected to the gate line 76.

The signal processing unit 82 is equipped with a sample/hold circuit 84 for each of the individual data lines 78. The electric charge signals that have been transmitted through the individual data lines 78 are held in the sample/hold circuits 84. The sample/hold circuit 84 is configured to include an op-amp 84A and a capacitor 84B and converts the electric charge signal into an analog voltage. Further, a switch 84C, which serves as a reset circuit that causes both electrodes of the capacitor 84B to short to cause the electric charge stored in the capacitor 84B to be discharged as a result of the switch 84C being switched ON, is disposed in the sample/hold circuit 84.

A multiplexer 86 and an A/D converter 88 are connected in order to an output side of the sample/hold circuits 84. The electric charge signals held in the individual sample/hold circuits 84 are converted into analog voltages, and the analog voltages are inputted in order (serially) to the multiplexer 86 and converted into digital image information by the A/D converter 88.

A frame memory 90 is connected to the signal processing unit 82 (see FIG. 4). The image information that has been outputted from the A/D converter 88 of the signal processing unit 82 is stored in order in the frame memory 90. The frame memory 90 has a storage capacity that is capable of storing one frame's worth of image information representing a radiographic image. Each time reading of electric charges is performed one line at a time, the one line's worth of image information that has been read is sequentially stored in the frame memory 90.

It will be noted that the radiation detector 60, the gate line driver 80, the signal processing unit 82 and the frame memory 90 pertaining to the present exemplary embodiment correspond to an electronic circuit of the present invention.

The frame memory 90 is connected to a cassette control unit 92 that controls operation of the entire electronic cassette 32. The cassette control unit 92 is realized by a microcomputer, and an optical communication control unit 94 is connected to the cassette control unit 92. The optical communication control unit 94 is connected to the connection terminal 32A. The optical communication control unit 94 controls the transmission of various information between the electronic cassette 32 and an external device to which the electronic cassette 32 has been connected via the connection terminal 32A. The cassette control unit 92 is configured to be capable of transmitting and receiving various information with the external device via the optical communication control unit 94. The cassette control unit 92 stores later-described image capture control information received from the external device and initiates reading of the electric charges on the basis of that information.

Further, a nonvolatile memory 93 is connected to the cassette control unit 92. The nonvolatile memory 93 has a storage capacity that is capable of storing plural frames' worth of image information representing radiographic images. The one frame's worth of image information that has been stored in the frame memory 90 is read by the cassette control unit 92 and is stored in the nonvolatile memory 93. The nonvolatile memory 93 is, for example, configured by flash memory, a hard disk drive (HDD), a solid-state drive (SSD), or a memory card.

Further, a power supply unit 96 is disposed in the electronic cassette 32. The various circuits and elements mentioned above (the gate line driver 80, the signal processing unit 82, the frame memory 90, the optical communication control unit 94, and the microcomputer that functions as the cassette control unit 92) are actuated by power supplied from the power supply unit 96. The power supply unit 96 has a built-in battery (a rechargeable secondary battery) so as to not impair the portability of the electronic cassette 32. The power supply unit 96 supplies power to the various circuits and elements from the charged battery.

The console 42 is configured as a server computer. The console 42 is equipped with a display 100, which displays operation menus and radiographic images that have been captured, and an operation panel 102, which is configured to include plural keys and by which various information and operation instructions are inputted.

Further, the console 42 pertaining to the present exemplary embodiment is equipped with a central processing unit (CPU)

104 that controls operation of the entire device, a read-only memory (ROM) 106 in which various programs including a control program are stored beforehand, a random-access memory (RAM) 108 that temporarily stores various data, an HDD 110 that stores and holds various data, a display driver 112, an operation input detection unit 114, a communication interface (I/F) unit 116 that is connected to the connection terminal 42A, an optical communication control unit 118 that is connected to the connection terminal 42B, and an image signal output unit 120 that is connected to the connection terminal 42C. The display driver 112 controls the display of various information on the display 100. The operation input detection unit 114 detects states of operation with respect to the operation panel 102. The communication I/F unit 116 transmits and receives various information, such as later-described exposure conditions and state information of the image capturing device 34, with the image capturing device 34 via the connection terminal 42A and the communication cable 35. The optical communication control unit 118 transmits and receives various information, such as image capture control information and image information, with the electronic cassette 32 via the connection terminal 42B and the communication cable 43. The image signal output unit 120 outputs image signals to the display device 36 via the connection terminal 42C and the display cable 37.

The CPU 104, the ROM 106, the RAM 108, the HDD 110, the display driver 112, the operation input detection unit 114, the communication I/F unit 116, the optical communication control unit 118 and the image signal output unit 120 are interconnected via a system bus BUS. Consequently, the CPU 104 can access the ROM 106, the RAM 108 and the HDD 110. The CPU 104 controls the display of various information on the display 100 via the display driver 112, controls the transmission and reception of various information with the image capturing device 34 via the communication I/F unit 116, controls the transmission and reception of various information with the electronic cassette 32 via the optical communication control unit 118, and controls images displayed on the display device 36 via the image signal output unit 120. Further, the CPU 104 can grasp states of operation by a user with respect to the operation panel 102 via the operation input detection unit 114.

The image capturing device 34 is equipped with a radiation source 130 that outputs the radiation X, a communication I/F unit 132 that transmits and receives various information, such as exposure conditions and state information of the image capturing device 34, with the console 42, and a radiation source control unit 134 that controls the radiation source 130 on the basis of received exposure conditions. The radiation source control unit 134 is also realized by a microcomputer. The radiation source control unit 134 stores the received exposure conditions and causes the radiation source 130 to irradiate the patient 30 with the radiation X on the basis of the stored exposure conditions.

Further, the display device 36 is equipped with a display unit 36A that displays images represented by received image signals.

Next, overall operation of the RIS 10 pertaining to the first exemplary embodiment will be briefly described.

One of the input terminals 12 (see FIG. 1) receives an image capture request from one of the doctors 26 or a radiologic technologist. In the image capture request, there are designated the date and time of image capture by the electronic cassette 32 and image capture conditions (the area of the patient 30 of which an image is to be captured, the angle and number of exposures; tube voltage, tube current and irradiation time for irradiating the patient 30 with the radiation X; and size and sensitivity of the electronic cassette 32).

The input terminal 12 notifies the RIS server 14 of the content of the image capture request it has received. The RIS server 14 stores, in the database 28, the content of the image capture request of which it has been notified by the input terminal 12.

The console 42 accesses the RIS 14 to acquire the content of the image capture request from the RIS server 14 and display the content of the image capture request on the display 100 (see FIG. 2 and FIG. 4).

One of the doctors 26 or a radiologic technologist initiates capture of a radiographic image on the basis of the content of the image capture request displayed on the display 100.

For example, as shown in FIG. 2, when capture of a radiographic image of an affected area of the patient 30 lying on top of the operating table 46 is to be performed, one of the doctors 26 or a radiologic technologist disposes the electronic cassette 32 between the operating table 46 and the affected area of the patient 30 in accordance with the area and angle of image capture and disposes the image capturing device 34 over the affected area. Further, one of the doctors 26 or a radiologic technologist performs, with respect to the operation panel 102 of the console 42 in accordance with the area of the patient 30 of which an image is to be captured and image capture conditions, exposure condition designation operation to designate exposure conditions such as tube voltage, tube current and irradiation time when irradiating the patient 30 with the radiation X. When exposure preparation of the image capturing device 34 is completed, one of the doctors 26 or a radiologic technologist performs, with respect to the operation panel 102 of the console 42, image capture instruction operation to instruct image capture.

Figure 6:
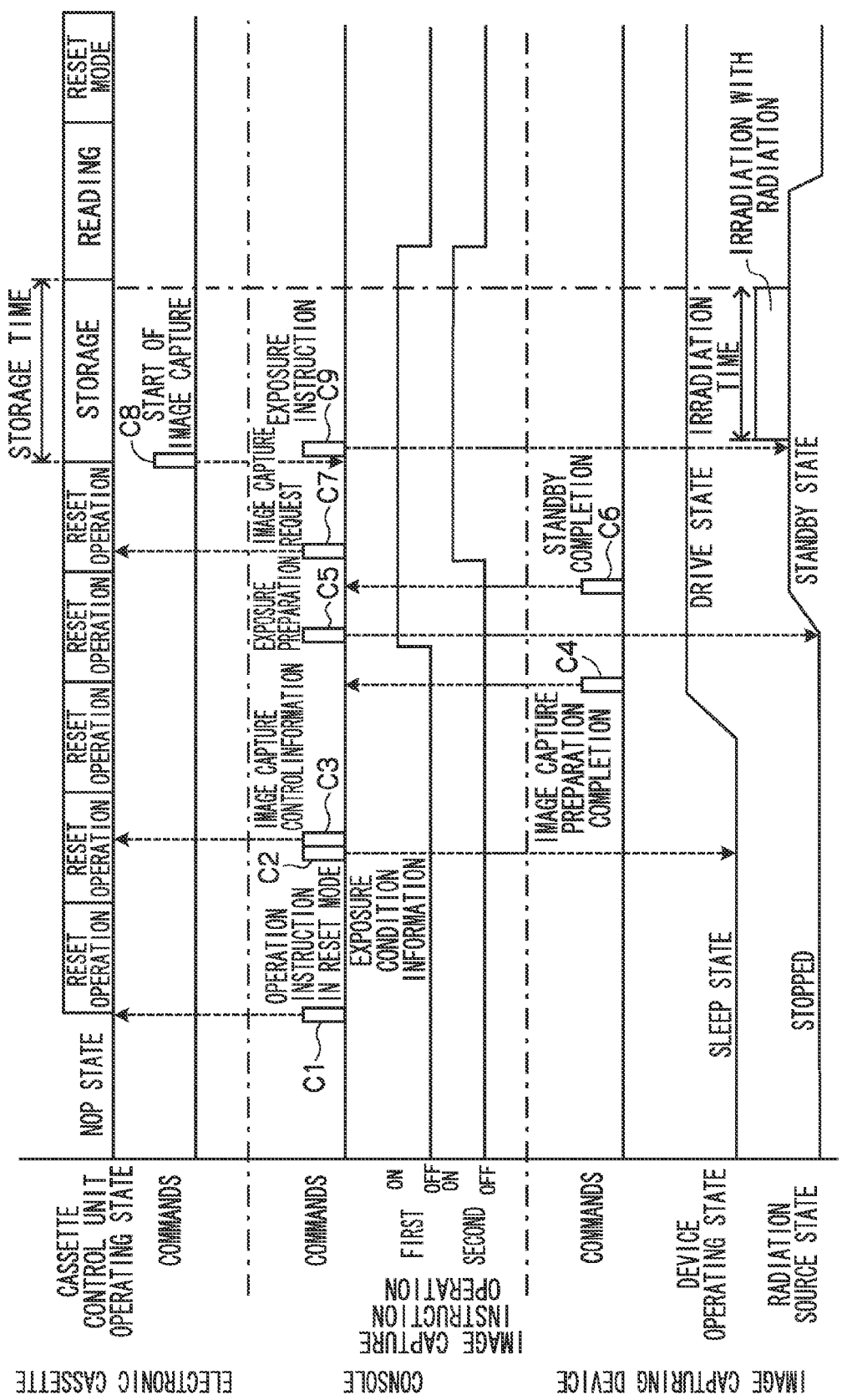
FIG. 6 is a timing chart showing a flow of operation when capturing a radiographic image pertaining to the first exemplary embodiment of the invention.

Next, operation of the image capturing system 18 pertaining to the first exemplary embodiment will be described in detail. In FIG. 6, there is shown a timing chart showing a flow of operation when capturing a radiographic image with the image capturing system 18.

In a state where the power of the electronic cassette 32 has been switched ON (launched state), the operating mode of the electronic cassette 32 is in a non-operating state (NOP state), which is an initial state. The electronic cassette 32 operates on the basis of instruction information received from the console 42 via the communication cable 43.

Incidentally, when the power of the electronic cassette 32 is in an ON state, electric charges are stored in each of the storage capacitors 68 of the built-in radiation detector 60 (see FIG. 4) of the electronic cassette 32 by a dark current or the like even in a state where the radiation detector 60 has not been irradiated with the radiation X. For this reason, when the operating mode of the electronic cassette 32 is in the non-operating state, the cassette control unit 92 outputs an instruction signal instructing reset with respect to the signal processing unit 82. When the instruction signal instructing reset is inputted to the signal processing unit 82, the switches 84C (see FIG. 5) switch ON to cause both electrodes of each of the capacitors 84B to short. By causing both electrodes of each of the capacitors 84B to short in this manner, electric charges stored unnecessarily in the capacitors 84B are released.

When the electronic cassette 32 is connected to the communication cable 43, the console 42 transmits, to the electronic cassette 32 via the communication cable 43, instruction information C1 instructing operation in a reset mode.

When the cassette control unit 92 receives the instruction information C1 instructing operation in the reset mode, the cassette control unit 92 moves the operating mode to the reset mode. The cassette control unit 92 controls the gate line driver 80 to cause the gate line driver 80 to output an ON signal to each of the gate lines 76 in order one line at a time. Each of the TFTs 70 connected to each of the gate lines 76 switches ON in order one line at a time. Thus, the electric charges stored in each of the storage capacitors 68 in order one line at a time flow out to each of the data lines 78 as electric charge signals. While the operating mode is in the reset mode, the cassette control unit 92 repeats reset operation to cause ON signals to be outputted to each of the gate lines 76 in order one line at a time and reset one frame's worth of electric charges stored in each of the storage capacitors 68.

When exposure condition designation operation is performed with respect to the operation panel 102, the console 42 transmits, to the image capturing device 34 via the communication cable 35, exposure condition information C2 such as tube voltage, tube current and exposure time designated by the exposure condition designation operation. Further, the console 42 transmits, to the electronic cassette 32 via the communication cable 43, image capture control information C3 such as storage time that causes electric charges to be stored in each of the storage capacitors 68 of the radiation detector 60 at the time of capture of a radiographic image.

When the power of the image capturing device 34 is switched ON and predetermined initial startup operation is completed, the operating state of the image capturing device 34 is placed in a sleep state and the image capturing device 34 stands by. When the image capturing device 34 receives the exposure condition information C2, the image capturing device 34 stores the exposure condition information it has received and moves its operating state to a drive state. When the operating state of the image capturing device 34 returns to the drive state, the image capturing device 34 transmits, to the console 42 via the communication cable 35, information C4 representing image capture preparation completion.

When the cassette control unit 92 of the electronic cassette 32 receives the image capture control information C3, the cassette control unit 92 stores the image capture control information it has received.

When the console 42 receives the information C4 representing image capture preparation completion, the console 42 displays on the display 100 the fact that image capture preparation has been completed. At this time, image capture instruction operation instructing image capture with respect to the operation panel 102 becomes possible. In the image capturing system 18 pertaining to the present exemplary embodiment, image capture instruction operation with respect to the operation panel 102 is configured as a two-stage operation. Capture of a radiographic image is performed as a result of a second stage of image capture instruction operation being performed after a first stage of image capture instruction operation. These two stages of image capture instruction operation may, for example, comprise pressing down two buttons on the operation panel 102 in order or may, for example, comprise half-pressing and fully pressing one button.

When the first stage of image capture instruction operation is performed with respect to the operation panel 102, the console 42 transmits, to the image capturing device 34 via the communication cable 35, instruction information C5 instructing exposure preparation.

When the image capturing device 34 receives the instruction information C5 instructing exposure preparation, the image capturing device 34 waits on the radiation source 130 (stands by) such that exposure at the tube voltage and the tube current represented by the exposure condition information stored immediately before is performed. When the image capturing device 34 completes waiting on the radiation source 130, the image capturing device 34 transmits, to the console 42 via the communication cable 35, information C6 representing standby completion.

When the console 42 receives the information C6 representing standby completion, the second stage of image capture instruction operation becomes possible. When the second stage of image capture instruction operation is performed with respect to the operation panel 102, the console 42 transmits, to the electronic cassette 32 via the communication cable 43, instruction information C7 requesting image capture.

When the cassette control unit 92 receives the instruction information C7 requesting image capture, the cassette control unit 92 performs reset operation until one frame's worth of reset operation is completed. After the completion of one frame's worth of reset operation, the cassette control unit 92 transmits, to the console 42 via the communication cable 43, instruction information C8 instructing image capture initiation and moves the operating mode to an image capturing mode.

When the console 42 receives the instruction information C8 instructing image capture initiation, the console 42 transmits, to the image capturing device 34 via the communication cable 35, instruction information C9 instructing exposure.

When the image capturing device 34 receives the instruction information C9 instructing exposure, the image capturing device 34 causes the radiation source 130 to irradiate the patient 30 with the radiation X for the amount of irradiation time represented by the exposure conditions stored immediately before.

The radiation X with which the patient 30 has been irradiated by the radiation source 130 is transmitted through the patient 30 and thereafter reaches the electronic cassette 32. Thus, electric charges corresponding to the radiation amount of the radiation X with which the electronic cassette 32 has been irradiated are stored in the storage capacitors 68 of each of the pixel components 74 of the radiation detector 60 built into the electronic cassette 32.

After the cassette control unit 92 transmits the instruction information C8 instructing image capture initiation, the cassette control unit 92 waits for the amount of storage time determined in the image capture control information stored immediately before and thereafter controls the gate line driver 80 to cause the gate line driver 80 to output ON signals to each of the gate lines 76 in order one line at a time. Each of the TFTs 70 connected to each of the gate lines 76 switches ON in order one line at a time. Thus, the electric charges stored in each of the storage capacitors 68 in order one line at a time flow out to each of the data lines 78 as electric charge signals. The electric charge signals flowing out to each of the data lines 78 are inputted to the individual sample/hold circuits 84 and are converted into analog voltage signals. The converted analog voltage signals are inputted in order (serially) to the multiplexer 86 and are converted into digital image information by the A/D converter 88, and the digital image information is stored in the frame memory 90.

Figure 7:
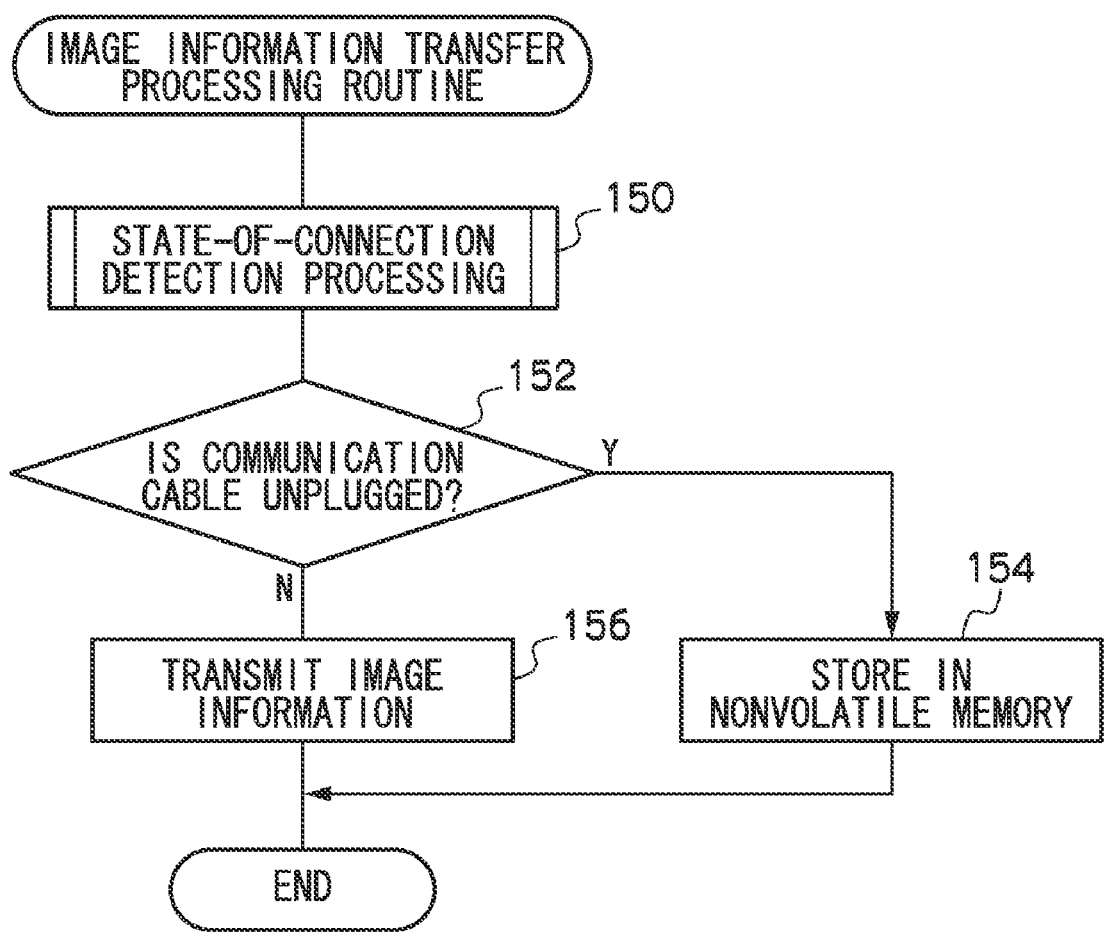
FIG. 7 is a flowchart showing the content of an image information transfer processing routine in the electronic cassette pertaining to the first exemplary embodiment of the invention.

When one frame's worth of image information is stored in the frame memory 90, the cassette control unit 92 executes a program that realizes an image information transfer processing routine shown in FIG. 7.

First, in step 150, the cassette control unit 92 detects the state of connection between the connection terminal 32A and the communication cable 43 by executing a later-described state-of-connection detection processing routine. Then, in step 152, the cassette control unit 92 determines whether or not the communication cable 43 is unplugged from the connection terminal 32A on the basis of the state of connection detected in step 150. When it has been determined that the communication cable 43 is unplugged from the connection terminal 32A, then in step 154, the cassette control unit 92 reads the one frame's worth of image information stored in the frame memory 90, stores the one frame's worth of image information in the nonvolatile memory 93, and ends the image information transfer processing routine.

On the other hand, when it has been determined in step 152 that the communication cable 43 is not unplugged from the connection terminal 32A, then in step 156, the cassette control unit 92 converts the one frame's worth of image information stored in the frame memory 90 into serial data and transmits the serial data to the console 42 via the communication cable 43. Then, the image information transfer processing routine ends.

When transfer of the one frame's worth of image information by the above-described image information transfer processing routine ends, the operating mode of the cassette control unit 92 moves to the reset mode. Here, the cassette control unit 92 does not perform serial radiography and moves to the reset mode, but the cassette control unit 92 may also perform serial radiography.

Incidentally, when the communication cable 43 is configured to be attachable and detachable as in the present exemplary embodiment, there are cases where, once it becomes easy for the communication cable 43 to be unplugged, the state of connection between the connection terminal 32A and the communication cable 43 becomes insecure and it becomes easier for unplugging of the cable to occur.

Thus, in the present exemplary embodiment, the cassette control unit 92 detects a bit error rate (BER) as information representing the state of connection between the connection terminal 32A and the communication cable 43. This bit error rate is the probability that bits that are different from transmission data will be included in reception data when transmitting and receiving digital data.

Figure 8:
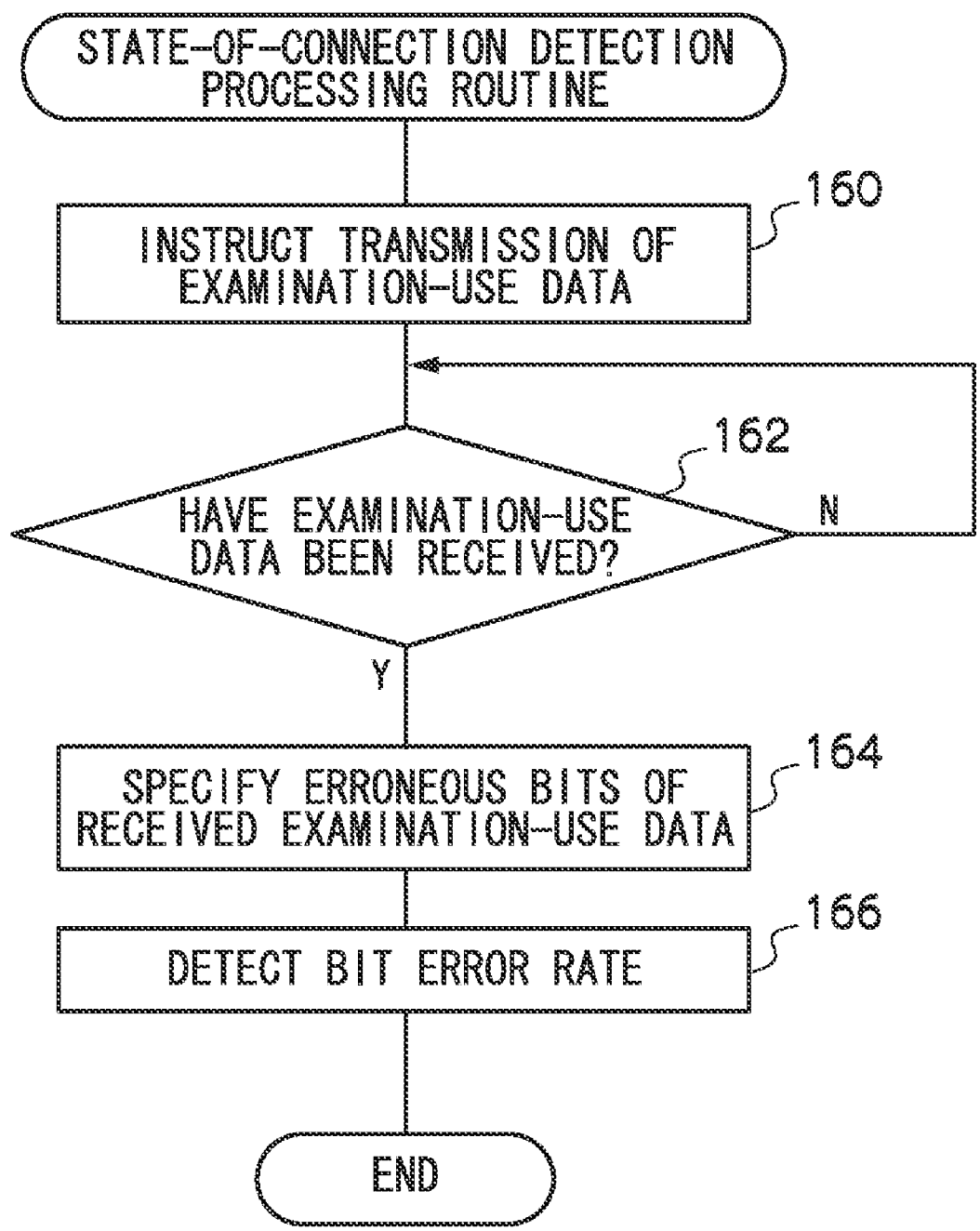
FIG. 8 is a flowchart showing the content of a state-of-connection detection processing routine in the electronic cassette pertaining to the first exemplary embodiment of the invention.

In the present exemplary embodiment, sets of same examination-use data determined beforehand are stored in the cassette control unit 92 of the electronic cassette 32 and in the ROM 106 of the console 42. When transmitting and receiving image information, the cassette control unit 92 of the electronic cassette 32 detects the bit error rate by executing a program that realizes, in the middle of executing the image information transfer processing routine, a state-of-connection detection processing routine shown in FIG. 8.

First, in step 160, the cassette control unit 92 transmits, to the console 42 via the communication cable 43, instruction information instructing transmission of the examination-use data determined beforehand.

When the console 42 receives the instruction information instructing transmission of the examination-use data, the console 42 transmits the examination-use data to the cassette control unit 92 via the communication cable 43.

In the next step 162, the cassette control unit 92 waits to receive the examination-use data, and in the next step 164, the cassette control unit 92 compares the received examination-use data with its own examination-use data stored beforehand to identify erroneous bits. In the next step 166, the cassette control unit 92 detects the bit error rate as information representing the state of connection by determining the ratio of the number of erroneous bits with respect to the number of bits of the examination-use data. Then, the state-of-connection detection processing routine ends.

In step 152 of the image information transfer processing routine, the cassette control unit 92 determines that the communication cable 43 is unplugged from the connection terminal 32A when the bit error rate detected in step 166 is equal to or greater than a threshold value. The cassette control unit 92 determines that the communication cable 43 is not unplugged from the connection terminal 32A when the bit error rate is less than the threshold value.

When the communication cable 43 had been unplugged from the connection terminal 32A of the electronic cassette 32, the communication cable 43 is reconnected to the connection terminal 32A by one of the doctors 26 or a radiologic technologist after the end of image capture. At this time, the image information is stored in the nonvolatile memory 93 of the electronic cassette 32, so an image information transfer request signal is transmitted from the console 42 to the electronic cassette 32 via the communication cable 43 one frame's worth at a time.

Each time the cassette control unit 92 receives an image information transfer request signal, the cassette control unit 92 converts one frame's worth of image information stored in the nonvolatile memory 93 into serial data and transmits the serial data to the console 42 via the communication cable 43. When the cassette control unit 92 transmits all of the image information stored in the nonvolatile memory 93, the cassette control unit 92 finally transmits transfer completion information representing completion of the transfer of the image information. When the console 42 receives the transfer completion information, the console 42 stops transmitting image information transfer request signals.

When the console 42 receives one frame's worth of image information, the console 42 performs predetermined image processing with respect to the one frame's worth of image information and causes the image information after image processing to be stored in the HDD 110 in a state where that image information after image processing has been associated with patient information of the patient 30. Further, the console 42 outputs image signals representing a radiographic image after image processing to the display device 36 and causes the radiographic image to be displayed on the display unit 36A of the display device 36. The doctors 26 perform surgery while checking the radiographic image displayed on the display unit 36A.

As described above, according to the first exemplary embodiment, even when it has been determined that the communication cable 43 is unplugged from the connection terminal 32A on the basis of the bit error rate in communication with the console 42, a radiographic image can be smoothly captured, without interrupting image capture, by causing the image information representing a radiographic image that has been generated to be stored in the nonvolatile memory 93.

In the preceding exemplary embodiment, a case has been described where the cassette control unit 92 detects the bit error rate as information representing the state of connection between the connection terminal 32A and the communication cable 43, but the present invention is not limited to this. The cassette control unit 92 may also be configured to detect any information as long as the information represents communication quality when data have been transmitted. For example, the cassette control unit 92 may be configured to detect, as information representing communication quality, the number of times retransmission is requested when transmitting data. There is a tendency for the number of times retransmission is requested to increase when the state of connection between the connection terminal 32A and the communication cable 43 worsens. For this reason, the number of times retransmission is requested can be used to determine the state of connection between the connection terminal 32A and the communication cable 43.

Next, a second exemplary embodiment will be described. It will be noted that identical reference numerals will be given to portions having the same configurations as those in the first exemplary embodiment and that description of those portions will be omitted.

The second exemplary embodiment differs from the first exemplary embodiment mainly in that the cassette control unit 92 measures the resistance value of a shield line of the communication cable 43 to determine the state of connection between the connection terminal 32A and the communication cable 43.

When the communication cable 43 includes a shield line for protecting a transmission line through which data are transmitted from noise and external damage, there is a tendency for the resistance value of the shield line to increase when the state of connection between the connection terminal 32A and the communication cable 43 worsens.

Thus, in the present exemplary embodiment, the cassette control unit 92 determines the resistance value of the shield line as information representing the state of connection between the connection terminal 32A and the communication cable 43 to determine the state of connection between the connection terminal 32A and the communication cable 43.

Figure 9:
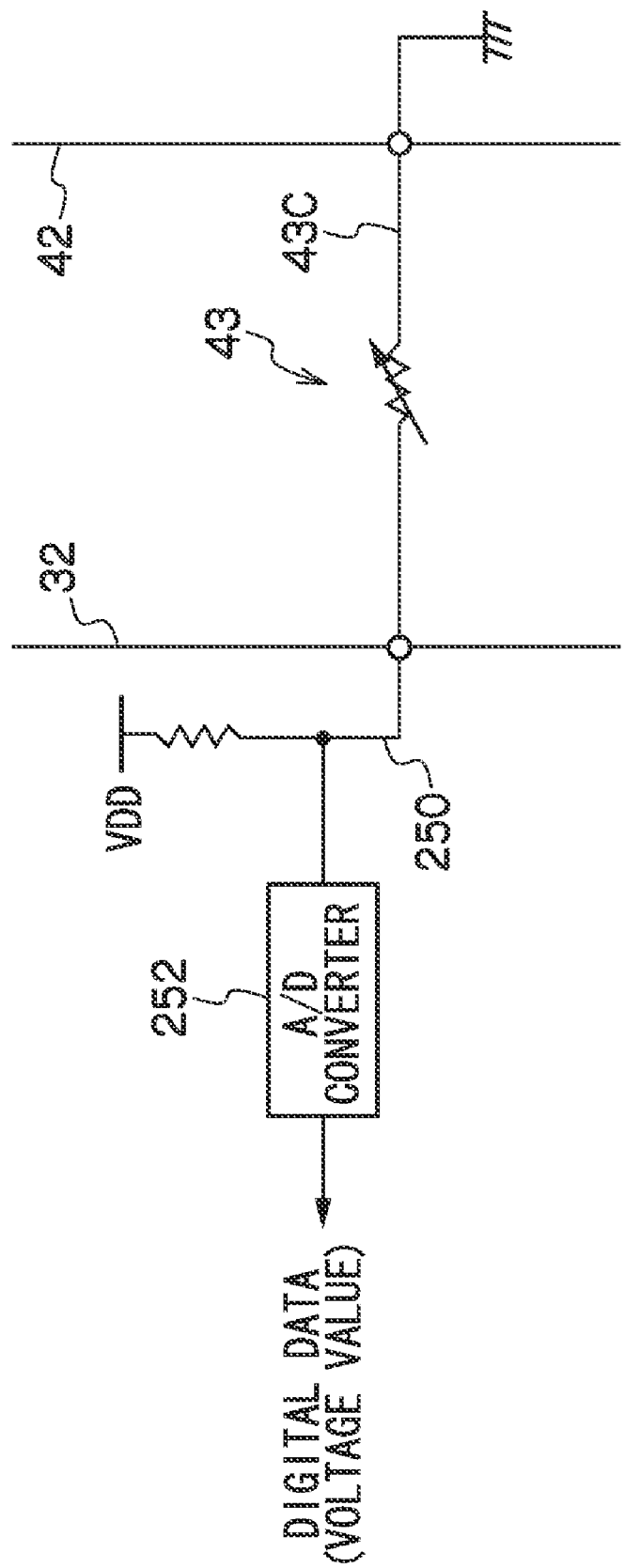
FIG. 9 is a circuit diagram showing one example of a measurement circuit that measures the resistance value of a shield line built into a communication cable pertaining to a second exemplary embodiment of the invention.

In FIG. 9, there is shown one example of a measurement circuit that measures the resistance value of a shield line 43C of the communication cable 43. In the case of the communication cable 43 that performs optical communication, the shield line 43C can be regarded as a single wire. Thus, one end of the shield line 43C is connected to a ground wire on the console 42 side, and the other end of the shield line 43C is connected to a wire 250 on the electronic cassette 32 side. Further, in the electronic cassette 32, current flows via the wire 250, the voltage level of the wire 250 is converted into digital data by an A/D converter 252, and the digital data are outputted to the cassette control unit 92. In this measurement circuit, when the resistance value of the shield line 43C increases, the voltage level of the wire 250 also rises. Thus, the cassette control unit 92 can determine the resistance value of the shield line 43C by detecting the voltage level of the wire 250.

The cassette control unit 92 determines whether or not the resistance value of the shield line 43C that has been determined is equal to or greater than a threshold value. When the resistance value of the shield line 43C that has been determined is equal to or greater than the threshold value, the cassette control unit 92 determines that the communication cable 43 is unplugged from the connection terminal 32A. On the other hand, when the resistance value of the shield line 43C that has been determined is less than the threshold value, the cassette control unit 92 determines that the communication cable 43 is not unplugged from the connection terminal 32A.

It will be noted that the other configurations and action of the radiology information system 10 pertaining to the second exemplary embodiment are the same as those of the first exemplary embodiment, so description thereof will be omitted.

In this manner, even when it has been determined that the communication cable 43 is unplugged from the connection terminal 32A on the basis of the resistance value of the shield line 43C of the communication cable 43 connected to the electronic cassette 32, a radiographic image can be smoothly captured, without interrupting image capture, by causing the image information representing a radiographic image that has been generated to be stored in the nonvolatile memory 93.

Figure 10:
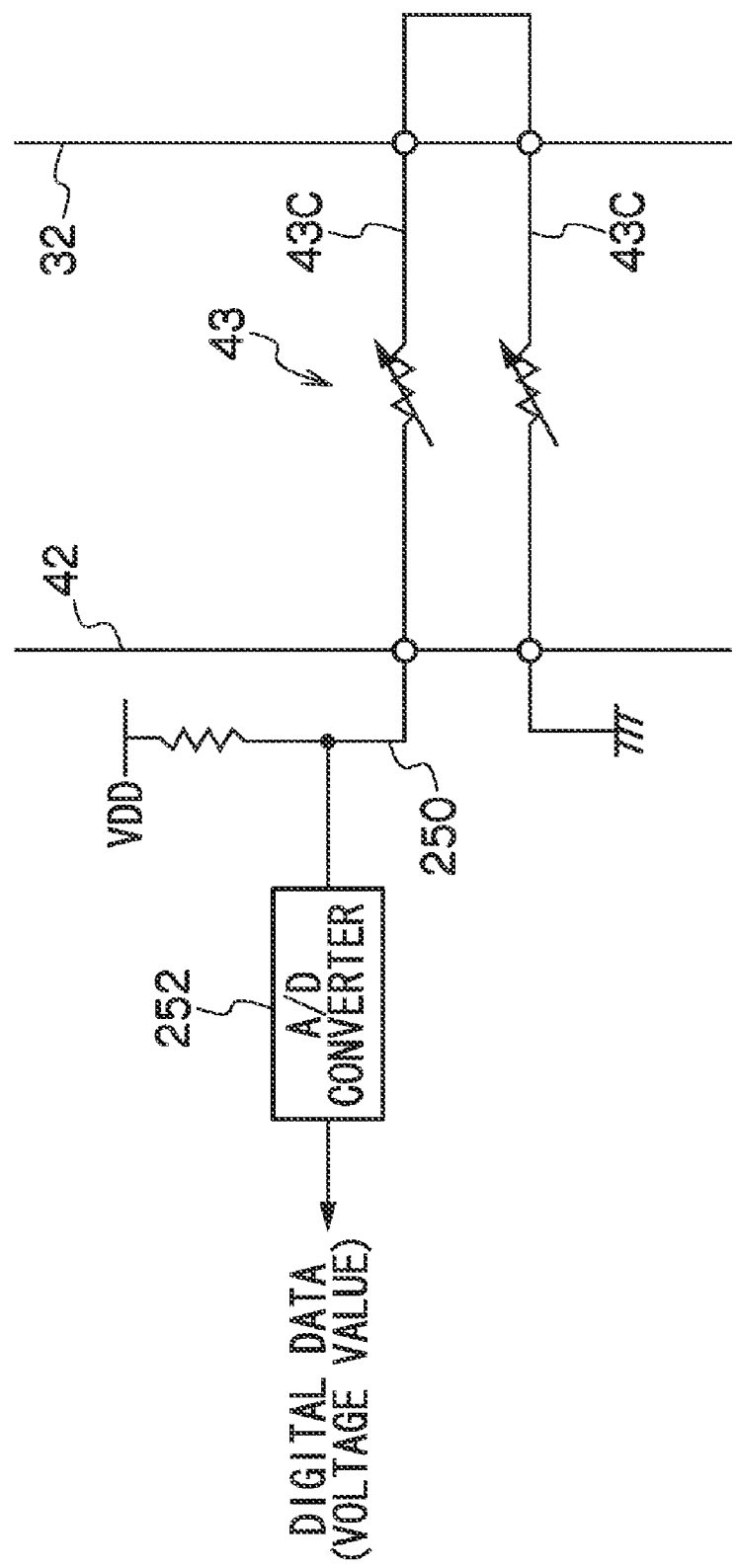
FIG. 10 is a circuit diagram showing one example of a measurement circuit that measures the resistance values of shield lines built into the communication cable pertaining to another exemplary embodiment.

In the preceding exemplary embodiment, the communication cable 43 may also be configured to use twisted pair lines as the communication cable 43. In this case, as shown in FIG. 10, as for the twisted pair lines, shield lines 43C are also disposed in a pair. One end side of each of the pair of shield lines 43C are interconnected to form a closed circuit, and the cassette control unit 92 detects the resistance values of the pair of shield lines 43C of the communication cable 43 at one time. Further, in a case where the communication cable 43 is equipped with one shield line 43C and one signal line each, for example, a switch that interconnects the signal line and the shield line 43C is disposed on one end side. While the cassette control unit 92 measures the resistance value, the cassette control unit 92 switches ON the switch to interconnect the signal line and the shield line 43C on the one end side and form a closed circuit. When performing data transmission in the signal line, the cassette control unit 92 switches OFF the switch to cut off the signal line and the shield line 43C.

Next, a third exemplary embodiment will be described. It will be noted that identical reference numerals will be given to portions having the same configurations as those in the first exemplary embodiment and that description of those portions will be omitted.

The third exemplary embodiment differs from the first exemplary embodiment mainly in that a mechanical switch 356 is disposed in the connection portion of the connection terminal 32A of the electronic cassette 32 and in that the cassette control unit 92 determines the state of connection between the connection terminal 32A and the communication cable 43 on the basis of an ON or OFF state of the mechanical switch 356.

Figure 11A:
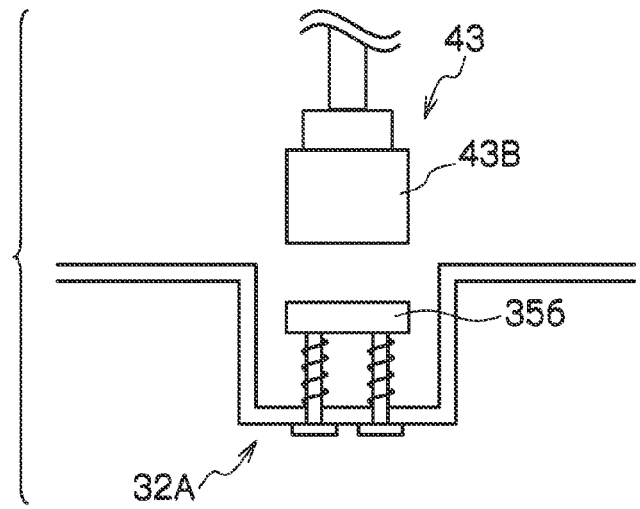
FIG. 11A is a diagram showing a state of a mechanical switch when the communication cable is not connected to a connection terminal.
Figure 11B:
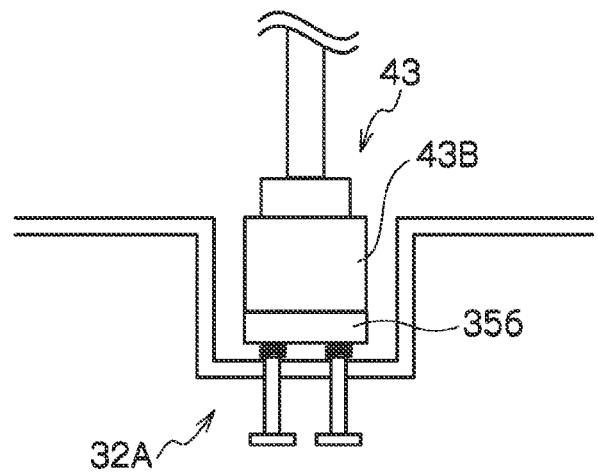
FIG. 11B is a diagram showing a state of the mechanical switch when the communication cable is connected to the connection terminal.

In the electronic cassette 32 pertaining to the third exemplary embodiment, as shown in FIG. 11A and FIG. 11B, the mechanical switch 356 is disposed in a portion of the connection terminal 32A that connects to a terminal 43B of the communication cable 43. The ON or OFF state of the mechanical switch 356 is outputted to the cassette control unit 92.

The cassette control unit 92 determines the state of connection between the connection terminal 32A and the communication cable 43 on the basis of the ON or OFF state of the mechanical switch 356 that has been inputted. As shown in FIG. 11A, when the mechanical switch 356 is OFF, it is determined that the communication cable 43 is unplugged from the connection terminal 32A. As shown in FIG. 11B, when the mechanical switch 356 is ON, it is determined that the communication cable 43 is not unplugged from the connection terminal 32A.

Figure 11C:
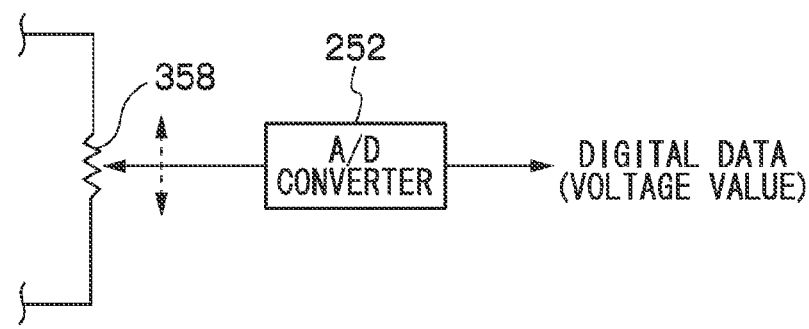
FIG. 11C is an equivalent circuit diagram of the mechanical switch.

There is a tendency for the press-down amount of the mechanical switch 356 (the insertion amount of the communication cable 43) to decrease when the state of connection between the connection terminal 32A and the communication cable 43 worsens. Thus, a circuit that detects the ON or OFF state of the mechanical switch 356 is configured as shown in FIG. 11C. For example, a resistor 358 is disposed inside the connection terminal 32A such that the insertion direction of the communication cable 43 and the current direction become identical. Moreover, the circuit is configured such that the detection position of voltage in the resistor 358 changes depending on the insertion amount of the communication cable 43. The circuit outputs an analog voltage signal that has been detected to the cassette control unit 92 via the A/D converter 252. The cassette control unit 92 determines the insertion amount of the communication cable 43 and determines the ON or OFF state of the mechanical switch 356 on the basis of the inputted signal.

It will be noted that the other configurations and action of the radiology information system 10 pertaining to the third exemplary embodiment are the same as those of the first exemplary embodiment, so description thereof will be omitted.

In this manner, even when it has been determined that the communication cable 43 is unplugged from the connection terminal 32A on the basis of the ON or OFF state of the mechanical switch 356 disposed in the connection terminal 32A of the electronic cassette 32, a radiographic image can be smoothly captured, without interrupting image capture, by causing the image information representing a radiographic image that has been generated to be stored in the nonvolatile memory.

In the preceding exemplary embodiment, a case where the mechanical switch 356 is disposed in the connection portion of the connection terminal 32A has been taken as an example and described, but the present invention is not limited to this. It suffices as long as the mechanical switch 356 is disposed in a portion where the communication cable 43 is positioned in a state where the communication cable 43 is connected to the connection terminal 32A.

Further, the cassette control unit 92 may also be configured to detect chattering of the mechanical switch 356 and determine the state of connection between the connection terminal 32A and the communication cable 43 after the communication cable 43 has been connected to the connection terminal 32A.

Figure 12A:
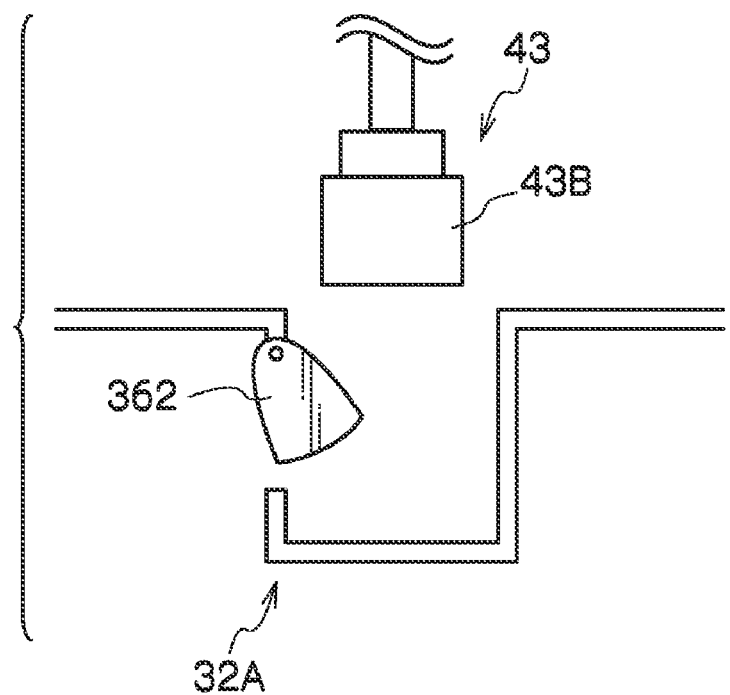
FIG. 12A is a diagram showing a state of an oscillating mechanical switch when the communication cable is not connected to the connection terminal.
Figure 12B:
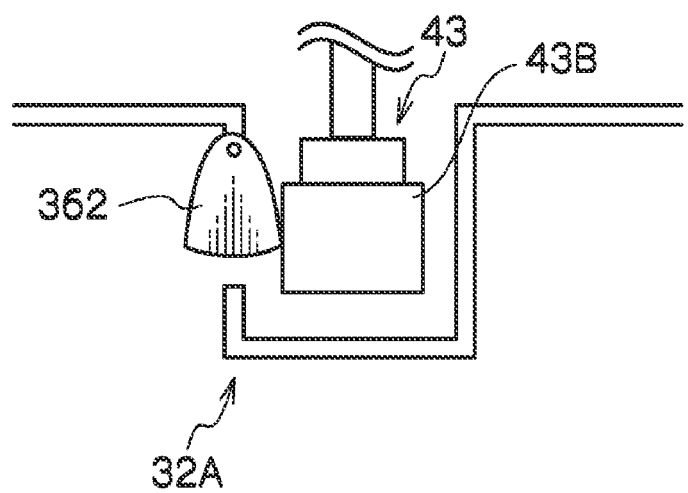
FIG. 12B is a diagram showing a state of the oscillating mechanical switch when the communication cable is connected to the connection terminal.

Further, as shown in FIG. 12A and FIG. 12B, the third exemplary embodiment may also be configured such that a mechanical switch 362 that oscillates in response to the insertion amount of the communication cable 43 is disposed in the connection terminal 32A. FIG. 12A shows a state of the mechanical switch 362 when the communication cable 43 is not connected to the connection terminal 32A. FIG. 12B shows a state of the mechanical switch 362 when the communication cable 43 is connected to the connection terminal 32A. Here, the cassette control unit 92 determines the state of connection between the connection terminal 32A and the communication cable 43 on the basis of the state of the mechanical switch 362.

Next, a fourth exemplary embodiment will be described. It will be noted that identical reference numerals will be given to portions having the same configurations as those in the first exemplary embodiment and that description of those portions will be omitted.

The fourth exemplary embodiment differs from the first exemplary embodiment mainly in that a holding member 458 for holding the connected communication cable 43 is disposed in the electronic cassette 32 and in that the cassette control unit 92 determines the state of connection between the connection terminal 32A and the communication cable 43 on the basis of an ON or OFF state of a mechanical switch disposed in the holding member.

Figure 13:
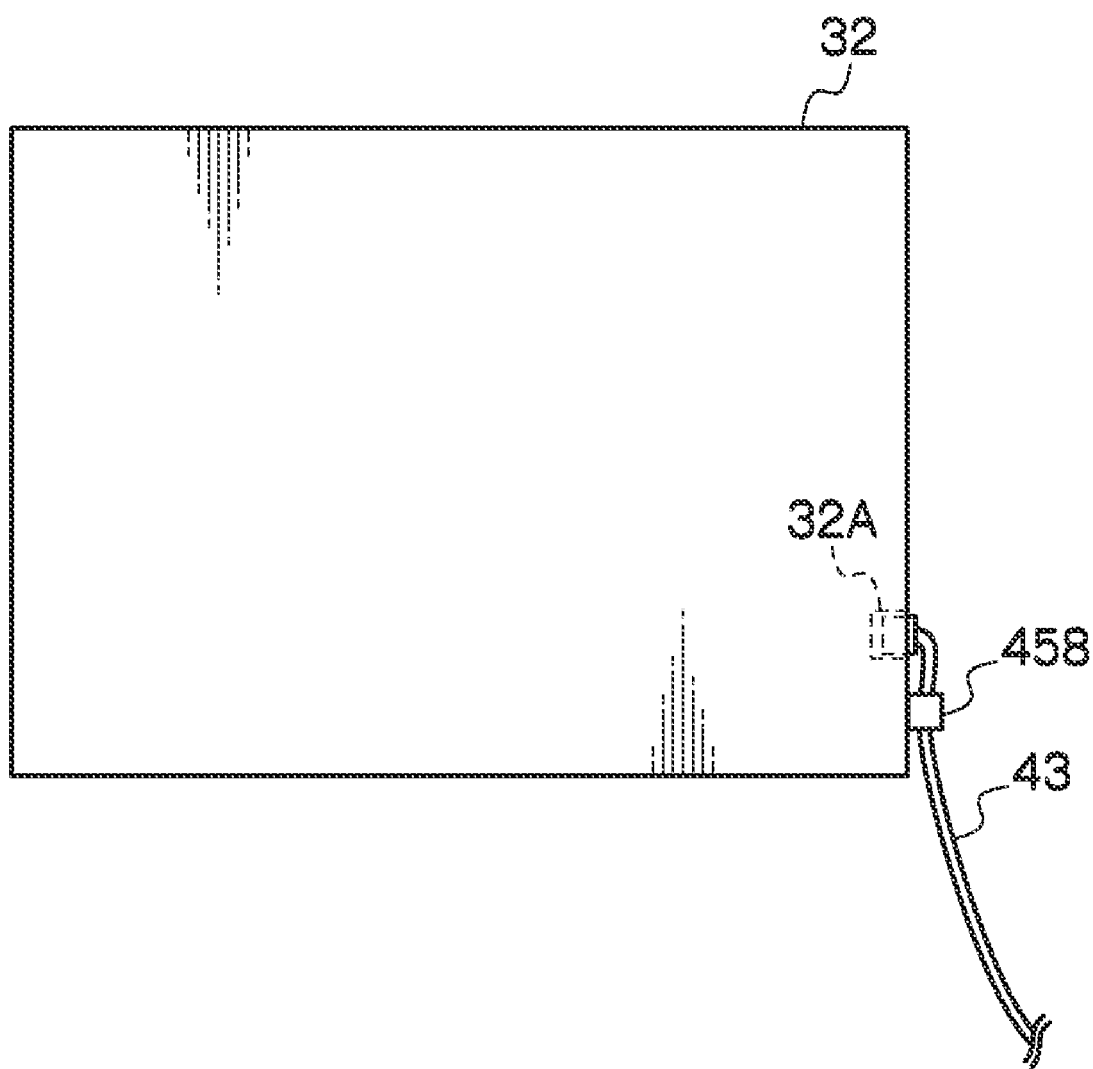
FIG. 13 is a diagram showing a state where the communication cable pertaining to a fourth exemplary embodiment is held by a holding member disposed in the electronic cassette.

The holding member 458 for holding the communication cable 43 in a state where the communication cable 43 has been connected to the connection terminal 32A is, as shown in FIG. 13, disposed on a side surface of the electronic cassette 32 pertaining to the fourth exemplary embodiment and in the vicinity of the connection terminal 32A. A mechanical switch (not shown) is disposed inside the holding member 458, and the ON or OFF state of the mechanical switch is outputted to the cassette control unit 92.

The cassette control unit 92 determines the state of connection between the connection terminal 32A and the communication cable 43 on the basis of the ON or OFF state of the mechanical switch of the holding member 458 that has been inputted. When the mechanical switch of the holding member 458 is OFF, it is judged that the communication cable 43 is not being held in the holding member 458, so it is determined that the communication cable 43 is unplugged from the connection terminal 32A. On the other hand, when the mechanical switch of the holding member 458 is ON, it is judged that the communication cable 43 is being held by the holding member 458, so it is determined that the communication cable 43 is not unplugged from the connection terminal 32A.

It will be noted that the other configurations and action of the radiology information system 10 pertaining to the fourth exemplary embodiment are the same as those of the first exemplary embodiment, so description thereof will be omitted.

In this manner, even when it has been determined that the communication cable 43 is unplugged from the connection terminal 32A on the basis of the ON or OFF state of the mechanical switch disposed in the holding member 458 for holding, in the electronic cassette 32, the connected communication cable 43, a radiographic image can be smoothly captured, without interrupting image capture, by causing the image information representing a radiographic image that has been generated to be stored in the nonvolatile memory.

Next, a fifth exemplary embodiment will be described. It will be noted that identical reference numerals will be given to portions having the same configurations as those in the first exemplary embodiment and that description of those portions will be omitted.

The fifth exemplary embodiment differs from the first exemplary embodiment mainly in that an optical sensor 566 is disposed in the connection portion of the connection terminal 32A of the electronic cassette 32 and in that the cassette control unit 92 determines the state of connection between the connection terminal 32A and the communication cable 43 on the basis of the detection result of the optical sensor 566.

Figure 14A:
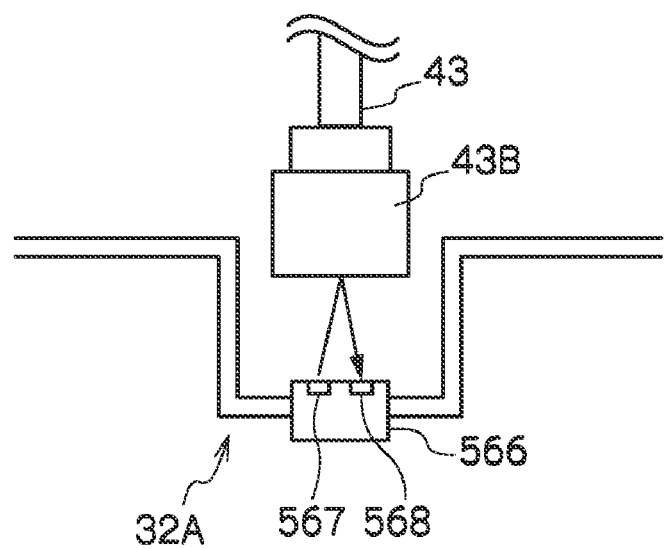
FIG. 14A is a diagram showing a state where a reflective sensor is disposed in the connection terminal.

The reflective sensor 566 is, as shown in FIG. 14A, disposed as an optical sensor in a portion of the connection terminal 32A of the electronic cassette 32 pertaining to the fifth exemplary embodiment that connects to the terminal 43B of the communication cable 43. The sensor 566 includes a light emitting component 567 that emits light in a direction where the terminal 43B of the communication cable 43 that is to be connected is positioned and a light receiving component 568 that receives the light reflected from the terminal 43B.

Figure 14B:
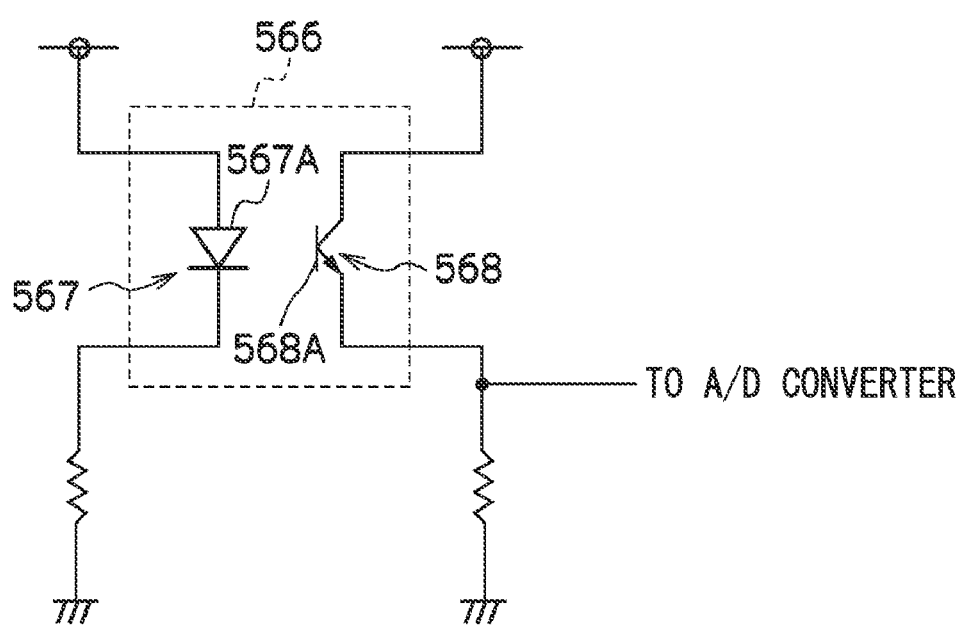
FIG. 14B is an equivalent circuit diagram of the reflective sensor.

In FIG. 14B, there is shown an equivalent circuit diagram of the sensor 566. The light emitting component 567 is equipped with a light emitting diode 567A, and the light receiving component 568 is equipped with a photodiode 568A. The voltage level or current level that flows via the photodiode 568A is converted into digital data by an A/D conversion component, and the digital data are outputted to the cassette control unit 92.

The cassette control unit 92 calculates the insertion amount of the communication cable 43 into the connection terminal 32A on the basis of the inputted digital data of the voltage level or current level. The cassette control unit 92 determines the state of connection between the connection terminal 32A and the communication cable 43 on the basis of the insertion amount that it has calculated.

It will be noted that the other configurations and action of the radiology information system 10 pertaining to the fifth exemplary embodiment are the same as those of the first exemplary embodiment, so description thereof will be omitted.

In this manner, even when it has been determined that the communication cable 43 is unplugged from the connection terminal 32A on the basis of the detection result of the optical sensor 566 disposed in the connection terminal 32A of the electronic cassette 32, a radiographic image can be smoothly captured, without interrupting image capture, by causing the image information representing a radiographic image that has been generated to be stored in the nonvolatile memory.

Next, a sixth exemplary embodiment will be described. It will be noted that identical reference numerals will be given to portions having the same configurations as those in the first exemplary embodiment and that description of those portions will be omitted.

The sixth exemplary embodiment differs from the first exemplary embodiment mainly in that an image information transfer request signal is transmitted from the console 42 to the electronic cassette 32 each time image capture of one frame's worth of image information ends and in that the cassette control unit 92 determines the state of connection between the connection terminal 32A and the communication cable 43 depending on whether or not the electronic cassette 32 has received an image information transfer request signal.

The console 42 pertaining to the sixth exemplary embodiment transmits an image information transfer request signal to the electronic cassette 32 via the communication cable 43 each time one frame's worth of image capture by the electronic cassette 32 ends.

Figure 15:
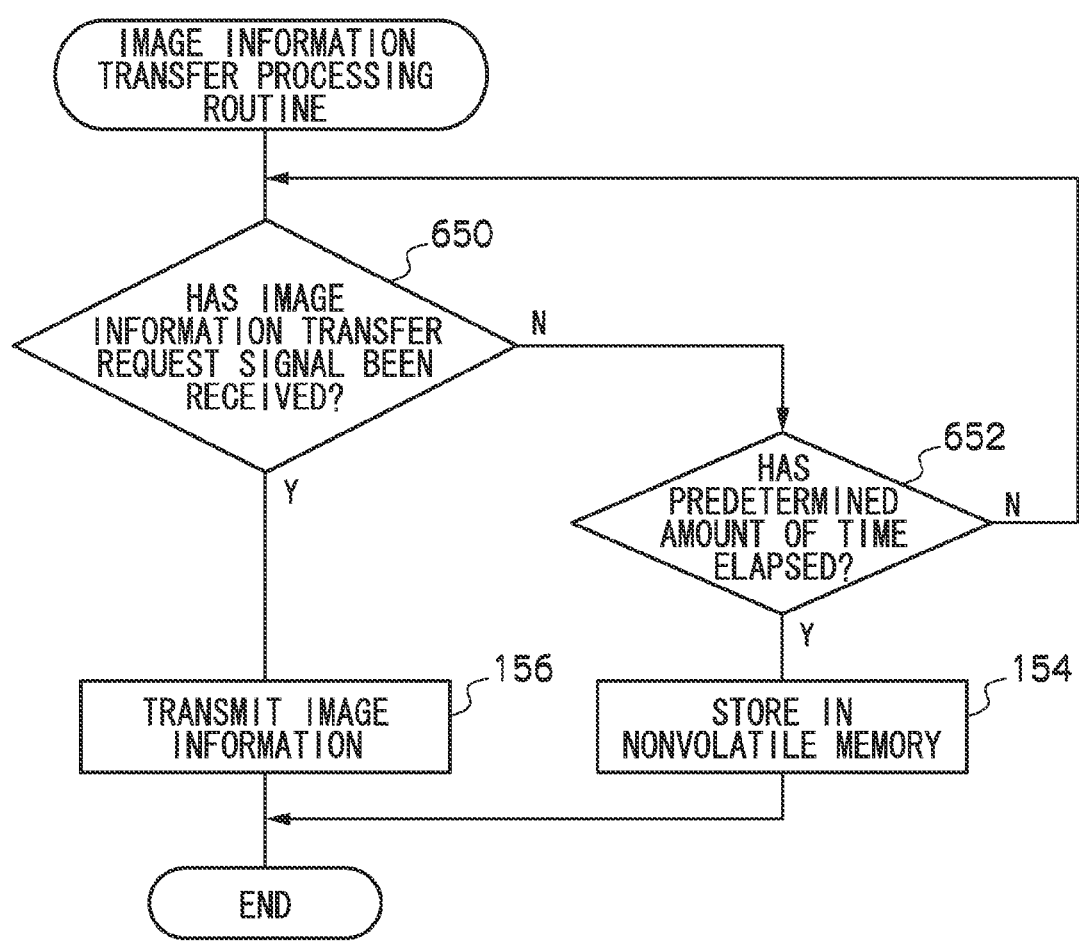
FIG. 15 is a flowchart showing the content of the image information transfer processing routine in the electronic cassette pertaining to a sixth exemplary embodiment of the invention.

The cassette control unit 92 of the electronic cassette 32 pertaining to the sixth exemplary embodiment executes a program that realizes an image information transfer processing routine shown in FIG. 15 when one frame's worth of image information is stored in the frame memory 90. It will be noted that identical reference numerals will be given to processing steps that are the same as those in the first exemplary embodiment and that description of those processing steps will be omitted.

First, in step 650, the cassette control unit 92 determines whether or not it has received an image information transfer request signal from the console 42 via the communication cable 43. When the cassette control unit 92 has not received an image information transfer request signal, then in step 652, the cassette control unit 92 determines whether or not a predetermined amount of time has elapsed after one frame's worth of image capture has ended. When the predetermined amount of time has not elapsed, the cassette control unit 92 returns to step 650, but when it has been determined that the predetermined amount of time has elapsed, the cassette control unit 92 judges that the communication cable 43 is unplugged from the connection terminal 32A because an image information transfer request signal has not been received via the communication cable 43. Then, in step 154, the cassette control unit 92 reads the one frame's worth of image information stored in the frame memory 90 and stores the one frame's worth of image information in the nonvolatile memory 93. Then, the image information transfer processing routine ends.

On the other hand, in step 650, when the cassette control unit 92 has received an image information transfer request signal via the communication cable 43, the cassette control unit 92 judges that the communication cable 43 is not unplugged from the connection terminal 32A. Then, in step 156, the cassette control unit 92 transmits, to the console 42 via the communication cable 43, the one frame's worth of image information stored in the frame memory 90. Then, the image information transfer processing routine ends.

It will be noted that the other configurations and action of the radiology information system 10 pertaining to the sixth exemplary embodiment are the same as those of the first exemplary embodiment, so description thereof will be omitted.

In this manner, even when it has been determined that the communication cable 43 is unplugged from the connection terminal 32A on the basis of whether or not the electronic cassette 32 has received an image information transfer request signal from the console 42, a radiographic image can be smoothly captured, without interrupting image capture, by causing the image information representing a radiographic image that has been generated to be stored in the nonvolatile memory.

In the preceding exemplary embodiment, a case where the cassette control unit 92 determines the state of connection of the communication cable 43 on the basis of whether or not the electronic cassette 32 has received an image information transfer request signal has been taken as an example and described, but the present invention is not limited to this. The cassette control unit 92 may also be configured to determine the state of connection of the communication cable 43 on the basis of whether or not the electronic cassette 32 has received another signal that is not an image information transfer request signal from the console 42. For example, the cassette control unit 92 may also be configured to determine the state of connection of the communication cable 43 on the basis of whether or not the electronic cassette 32 has received a signal received from the console 42 at constant periods.

Further, in the preceding exemplary embodiment, a case where the electronic cassette 32 detects information representing the state of connection has been taken as an example and described, but the present invention is not limited to this. The invention may also be configured such that the console 42 detects, in the same manner as the case where the electronic cassette 32 detects information representing the state of connection, information representing the state of connection (communication quality, the resistance value of a shield line, the ON or OFF state of a switch, the detection result of a sensor, etc.) and transmits the detection result to the electronic cassette 32. In this case, the electronic cassette 32 may be configured to determine whether or not the communication cable 43 is unplugged from the connection terminal 32A on the basis of the detection result the electronic cassette 32 has received from the console 42.

Further, a case where the cassette control unit 92 causes the image information stored in the frame memory 90 to be stored in the nonvolatile memory 93 has been taken as an example and described, but the present invention is not limited to this. The cassette control unit 92 may also be configured to cause the image information stored in the frame memory 90 to be stored in a volatile memory.

Further, a case where each of the electronic cassette 32 and the image capturing device 34 transmits and receives various information via communication cables with the console 42 has been taken as an example and described, but the invention may also be configured such that each of the electronic cassette 32 and the image capturing device 34 transmits and receives various instruction information by wireless communication with the console 42.

Further, a case where the cassette control unit 92 detects information representing the state of connection after one frame's worth of image capture ends has been taken as an example and described, but the present invention is not limited to this. The invention may also be configured such that the cassette control unit 92 always detects information representing the state of connection between the connection terminal 32A and the communication cable 43 at constant periods. In this case, the cassette control unit 92 determines the state of connection between the connection terminal 32A and the communication cable 43 using the most recent detection result when one frame's worth of image capture has ended.

Next, a seventh exemplary embodiment will be described. It will be noted that identical reference numerals will be given to portions having the same configurations as those in the first exemplary embodiment and that description of those portions will be omitted.

Figure 16:
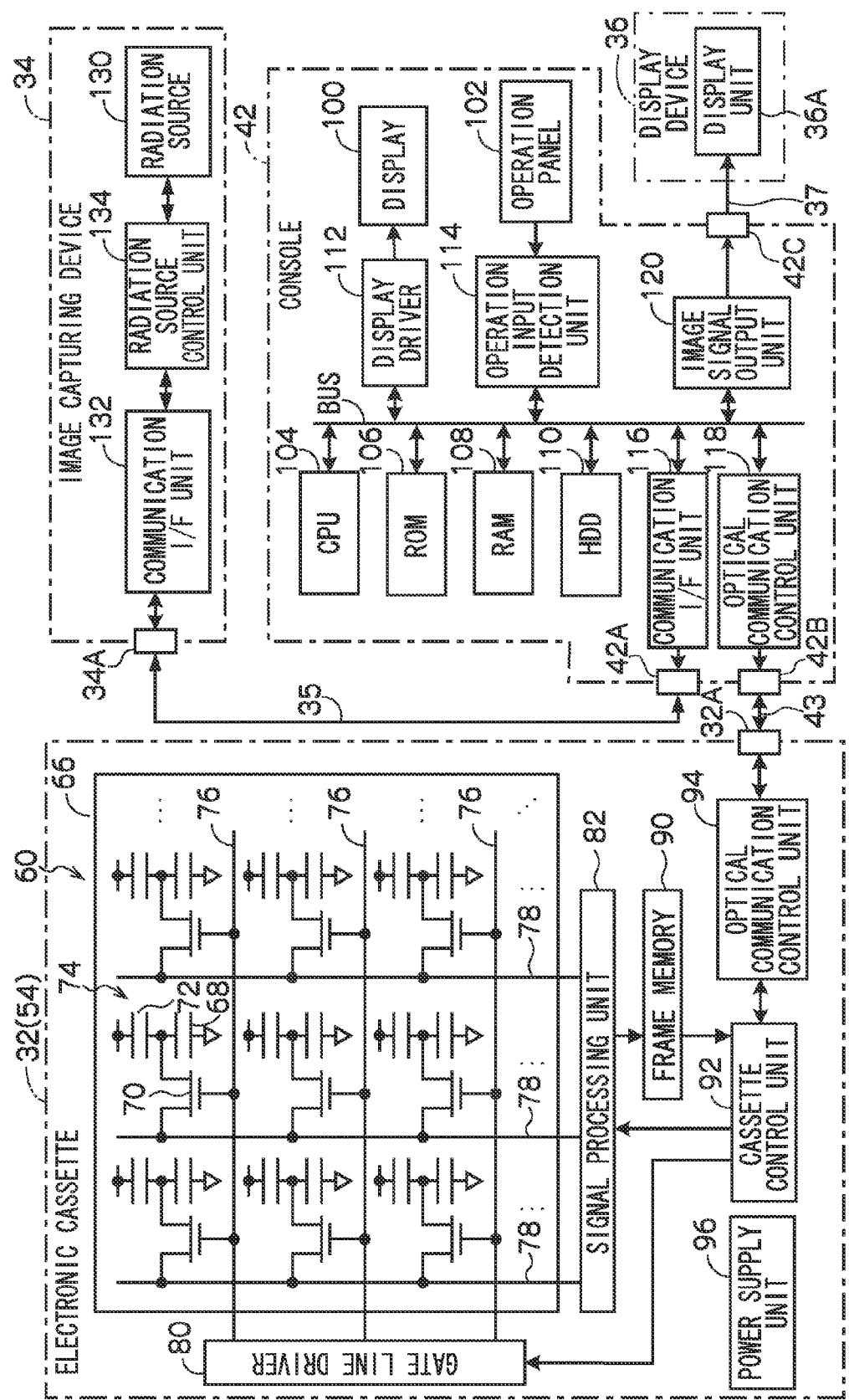
FIG. 16 is a block diagram showing the detailed configuration of a radiographic image capturing system pertaining to a seventh exemplary embodiment of the invention.

In FIG. 16, there is shown a block diagram showing the detailed configuration of a radiographic image capturing system 18 pertaining to the present exemplary embodiment.

A connection terminal 34A for performing communication with the console 42 is disposed in the image capturing device 34. A connection terminal 42A for performing communication with the image capturing device 34, a connection terminal 42B for performing communication with the electronic cassette 32 and a connection terminal 42C for outputting image signals to the display device 36 are disposed in the console 42.

The image capturing device 34 is connected to the console 42 via a communication cable 35, and the display device 36 is connected to the console 42 via a display cable 37. At the time of capture of a radiographic image, a communication cable 43 is connected to the connection terminal 32A of the electronic cassette 32, and the electronic cassette 32 is connected to the console 42 via the communication cable 43.

The radiation detector 60 built into the electronic cassette 32 is configured as a result of a photoelectric conversion layer that absorbs and converts the radiation X into electric charges being layered on a TFT active matrix substrate 66.

The electronic cassette 32 is equipped with a signal processing unit 82, a frame memory 90, a cassette control unit 92, an optical communication control unit 94 and a power supply unit 96. The optical communication control unit 94 is connected to the connection terminal 32A and controls the transmission of various information between the electronic cassette 32 and an external device to which the electronic cassette 32 has been connected via the connection terminal 32A. The cassette control unit 92 is configured to be capable of transmitting and receiving various information with the external device via the optical communication control unit 94. The cassette control unit 92 stores later-described image capture control information received from the external device and initiates reading of the electric charges on the basis of that information.

The console 42 is configured as a server computer. The console 42 is equipped with a display 100 and an operation panel 102.

Further, the console 42 pertaining to the present exemplary embodiment is equipped with a CPU 104, a ROM 106, a RAM 108, an HDD 110, a display driver 112, an operation input detection unit 114, a communication interface (I/F) unit 116, an optical communication control unit 118 and an image signal output unit 120.

The image capturing device 34 is equipped with a radiation source 130, a communication I/F unit 132 and a radiation source control unit 134.

Further, the display device 36 is equipped with a display unit 36A that displays images represented by received image signals.

Next, operation of the image capturing system 18 pertaining to the present exemplary embodiment will be described in detail.

As shown in the timing chart of FIG. 6, the image capturing system 18 performs operation that captures a radiographic image.

The console 42 transmits, to the electronic cassette 32 via the communication cable 43, an image information transfer request signal one line's worth at a time. Each time an image information transfer request signal is received, the cassette control unit 92 converts the one line's worth of image information stored in the frame memory 90 into serial data and transmits the serial data to the console 42 via the communication cable 43. The console 42 may be configured to count the number of lines that have been transferred and stop transmitting image information transfer request signals when the count value becomes a number of lines corresponding to one frame. Further, the cassette control unit 92 may be configured to finally transmit transfer completion information representing completion of the transfer of the one frame's worth of image information, and the console 42 may be configured to stop transmitting image information transfer request signals when the console 42 has received the transfer completion information.

When transfer of the one frame's worth of image information ends, the operating mode of the cassette control unit 92 moves to the reset mode. Here, the cassette control unit 92 moves to the reset mode without performing serial radiography. The cassette control unit 92 may also perform serial radiography.

The console 42 performs predetermined image processing with respect to the one frame's worth of image information and causes the image information after image processing to be stored in the HDD 110 in a state where that image information after image processing has been associated with patient information of the patient 30. Further, the console 42 outputs image signals representing a radiographic image after image processing to the display device 36 and causes the radiographic image to be displayed on the display unit 36A of the display device 36.

Incidentally, when the communication cable 43 is configured to be attachable and detachable as in the present exemplary embodiment, there are cases where, once the communication cable 43 is unplugged, the state of connection between the connection terminal 32A and the communication cable 43 becomes insecure and it becomes easy for unplugging of the cable to occur.

Thus, in the present exemplary embodiment, the cassette control unit 92 detects a bit error rate (BER) as state information representing the state of connection between the connection terminal 32A and the communication cable 43.

In the present exemplary embodiment, sets of same examination-use data determined beforehand are stored in the cassette control unit 92 of the electronic cassette 32 and in the ROM 106 of the console 42, and when transmitting and receiving image information, the console 42 detects the bit error rate by executing processing of a state-of-connection detection program.

Figure 17:
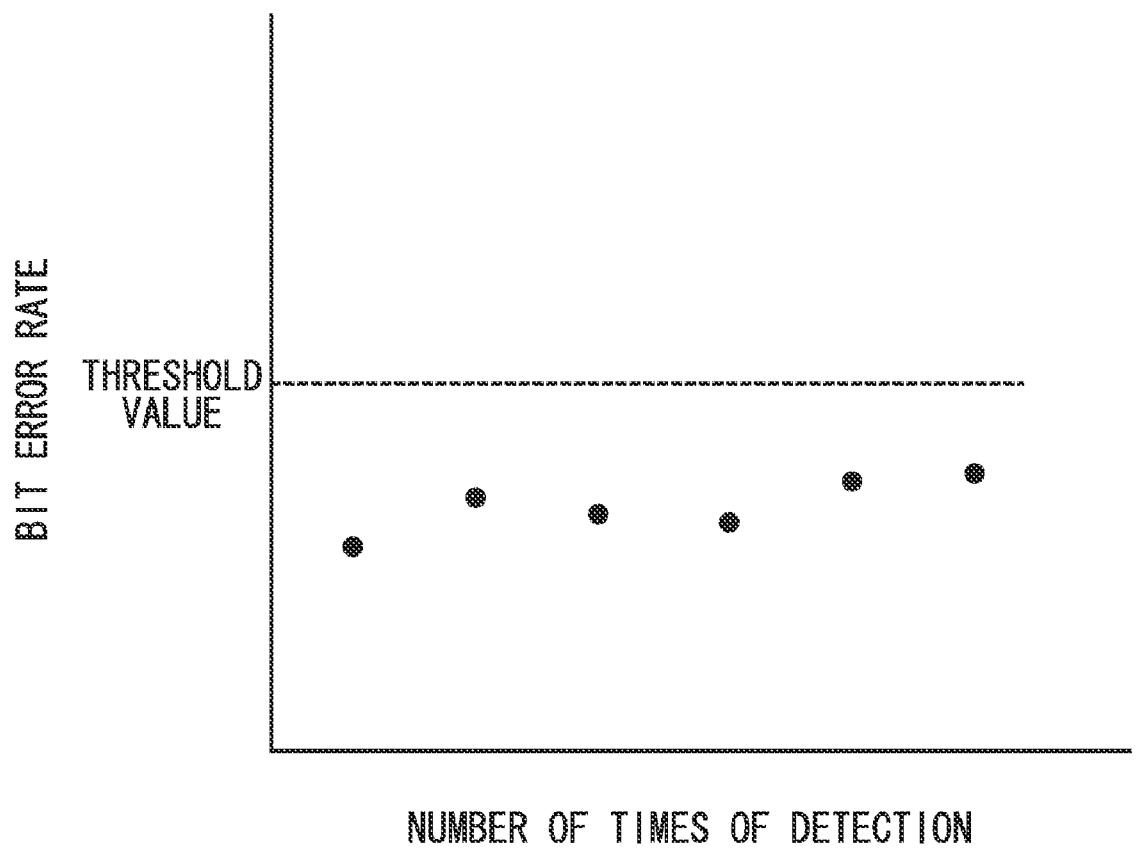
FIG. 17 is a graph showing one example of changes in a bit error rate.

In FIG. 17, there is shown a graph showing one example of changes in the bit error rate.

There is a tendency for the value of the bit error rate to become larger when the state of connection between the connection terminal 32A and the communication cable 43 worsens.

In the present exemplary embodiment, the bit error rate in a case where the state of connection between the connection terminal 32A and the communication cable 43 worsens and becomes inappropriate for the transmission of image information is experimentally determined and stored in the ROM 106 of the console 42 as a threshold value. The console 42 determines whether or not the communication cable 43 is inappropriate for the transmission of image information by executing processing of a transfer error occurrence prediction program at a predetermined timing in a preparatory stage of capturing a radiographic image. The predetermined timing beforehand may, for example, be a timing when the power of the console 42 is switched ON or a timing when the console 42 acquires information such as the content of an image capture request from the RIS server 14. Further, when the image capturing system 18 captures a radiographic image in an image capturing room, a sensor may be disposed in the door through which the patient 30 enters the image capturing room, and the predetermined timing may be a timing when the sensor detects that the patient 30 has entered the image capturing room. Moreover, in a case where the image capturing room is separate from a control room, a sensor may be disposed in the door between the image capturing room and the control room, and the predetermined timing may be a timing when the sensor detects that a technologist has entered the image capturing room.

Figure 18:
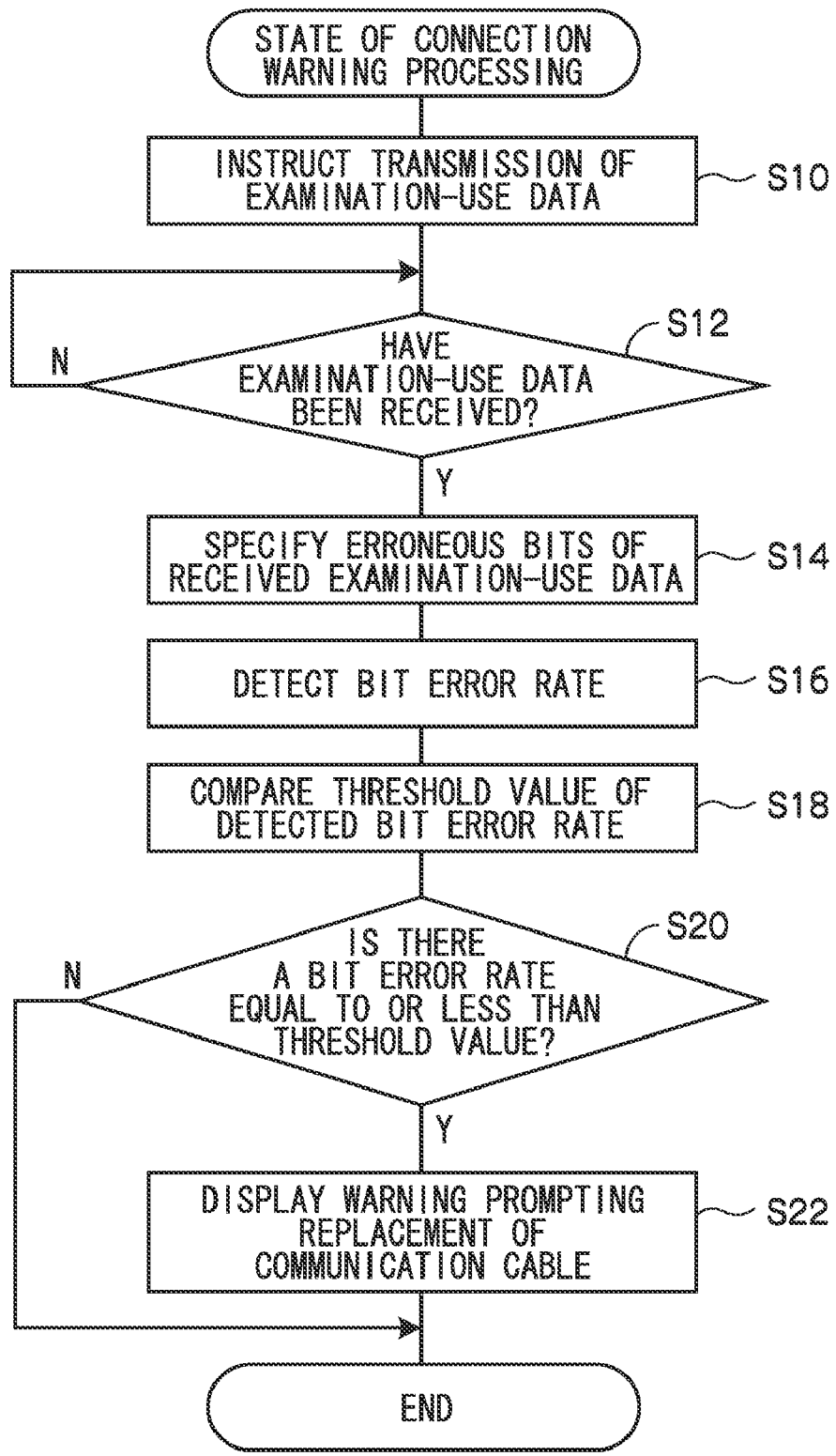
FIG. 18 is a flowchart showing a flow of processing of a state-of-connection warning processing program pertaining to the seventh exemplary embodiment of the invention.

In FIG. 18, there is shown a flowchart showing a flow of processing of a state-of-connection warning processing program that is executed by the CPU 104 at a predetermined timing in a preparatory stage of capturing a radiographic image. This program is stored beforehand in a predetermined region of the ROM 106.

In step S10, the CPU 104 transmits, to the electronic cassette 32 via the communication cable 43, instruction information instructing transmission of the examination-use data determined beforehand.

When the instruction information instructing transmission of the examination-use data is received, the electronic cassette 32 transmits the examination-use data to the console 42 via the communication cable 43.

In the next step S12, the CPU 104 waits to receive the examination-use data. In the next step S14, the CPU 104 compares the received examination-use data with its own examination-use data stored beforehand to identify erroneous bits. In the next step S16, the CPU 104 detects the bit error rate by determining the ratio of the number of erroneous bits with respect to the number of bits of the examination-use data.

In step S18, the CPU 104 compares the detected bit error rate with the threshold value stored in the ROM 106.

In the next step S20, the CPU 104 determines whether or not the bit error rate is equal to or greater than the threshold value. When the determination is YES, the CPU 104 moves to step S22. When the determination is NO, processing ends.

In step S22, the CPU 104 causes a warning prompting replacement of the communication cable 43 to be displayed on the display 100 for a predetermined amount of time. Then, processing ends.

When the warning prompting replacement of the communication cable 43 is displayed on the display 100, one of the doctors 26 or a radiologic technologist replaces the communication cable 43 with a new communication cable. Thus, the state of connection between the connection terminal 23A and the communication cable 43 becomes secure and the image information can be securely transferred. Consequently, a radiographic image can be smoothly captured.

As described above, according to the seventh exemplary embodiment, the console 42 acquires state information representing the state of connection between the connection terminal 32A of the electronic cassette 32 and the communication cable 43 and issues a warning when it has been determined on the basis of the acquired state information that the communication cable 43 connected to the connection terminal 32A is inappropriate for the transmission of image information, whereby a radiographic image can be smoothly captured.

In the preceding exemplary embodiment, a case has been described where the console 42 acquires, by detecting, state information representing the state of connection, but the present invention is not limited to this. For example, the invention may also be configured such that the electronic cassette 32 detects the state of connection and transmits state information representing the state of connection to the console 42. Further, for example, the invention may also be configured such that the threshold value is stored in the electronic cassette 32 or an external device.

Further, in the preceding exemplary embodiment, a case has been described where the console 42 detects the bit error rate as information representing the state of connection between the connection terminal 32A and the communication cable 43, but the present invention is not limited to this. The console 42 may also be configured to detect any information as long as the information represents communication quality when transmitting data. For example, the console 42 may be configured to detect, as information representing communication quality, the number of times retransmission is requested when transmitting data. There is a tendency for the number of times retransmission is requested to increase when the state of connection between the connection terminal 32A and the communication cable 43 worsens. For this reason, the number of times retransmission is requested can be used to determine the state of connection between the connection terminal 32A and the communication cable 43.

Further, for example, when the communication cable 43 includes a shield line for protecting the signal line through which data are transmitted from noise and external damage, the invention may be configured to measure the resistance value of the shield line. There is a tendency for the resistance value of the shield line to increase when the state of connection between the connection terminal 32A and the communication cable 43 worsens. For this reason, the resistance value of the shield line can be used to determine the state of connection between the connection terminal 32A and the communication cable 43. In FIG. 9, there is shown one example of a measurement circuit that measures the resistance value of a shield line 43C of the communication cable 43. In the case of the communication cable 43 that performs optical communication, the shield line 43C can be regarded as a single wire. Thus, for example, in the console 42, one end of the shield line 43C is connected to a ground wire. In the electronic cassette 32, current flows via the wire 250 with respect to the other end of the shield line 43C. The voltage level of the wire 250 is converted into digital data by an A/D converter 252 and is detected. In this case, the electronic cassette 32 transmits the voltage level that has been detected to the console 42. It will be noted that the invention may also be configured such that, in the electronic cassette 32, the other end of the shield line 43C may be connected to a ground wire and, in the console 43, the resistance value of the shield line 43C is detected. In this measurement circuit, when the resistance value of the shield line 43C increases, the voltage level of the wire 250 also rises. Thus, the resistance value of the shield line 43C can be determined by detecting the voltage level of the wire 250.

Further, for example, when twisted pair lines are used as the communication cable 43, as for the twisted pair lines, shield lines 43C are also disposed in a pair. In FIG. 10, there is shown one example of a measurement circuit that measures the resistance values of the shield lines 43C of the communication cable 43 in a case where the shield lines 43C are disposed in a pair in the communication cable 43. In this case, the resistance values of the pair of shield lines 43C can be detected at one time by interconnecting one end side of each of the pair of shield lines 43C to form a closed circuit. Further, in a case where the communication cable 43 is equipped with one shield line 43C and one signal line each, for example, a switch that interconnects the shield line 43C and the signal line is disposed on one end side. While the resistance value is measured, the switch is switched ON to interconnect the signal line and the shield line 43C on the one end side and form a closed circuit. When performing data transmission in the signal line, the switch is switched OFF to cut off the signal line and the shield line 43C.

Further, in the preceding exemplary embodiment, a case has been described where the console 42 detects communication quality as information representing the state of communication between the connection terminal 32A and the communication cable 43, but the present invention is not limited to this. For example, as shown in FIG. 11A and FIG. 11B, a mechanical switch or a sensor may be disposed in the connection terminal 32A. The invention may detect the physical state of connection between the connection terminal 32A and the communication cable 43 that has been detected by the mechanical switch or the sensor. Further, for example, when the position of contact with a resistor 358 changes because of the insertion amount of the communication cable 43 and the mechanical switch 356 outputs an analog signal as shown in FIG. 11C, the invention may detect that analog signal. As shown in FIG. 12A and FIG. 12B, as another example of a mechanical switch, the mechanical switch 362 that oscillates in response to the insertion amount of the communication cable 43 may also be disposed. This mechanical switch 362 can also be used to determine the state of connection between the connection terminal 32A and the communication cable 43. Moreover, as shown in FIG. 14A and FIG. 14B, the reflective sensor 566 may also be disposed as a sensor in the connection terminal 32A.

Figure 19:
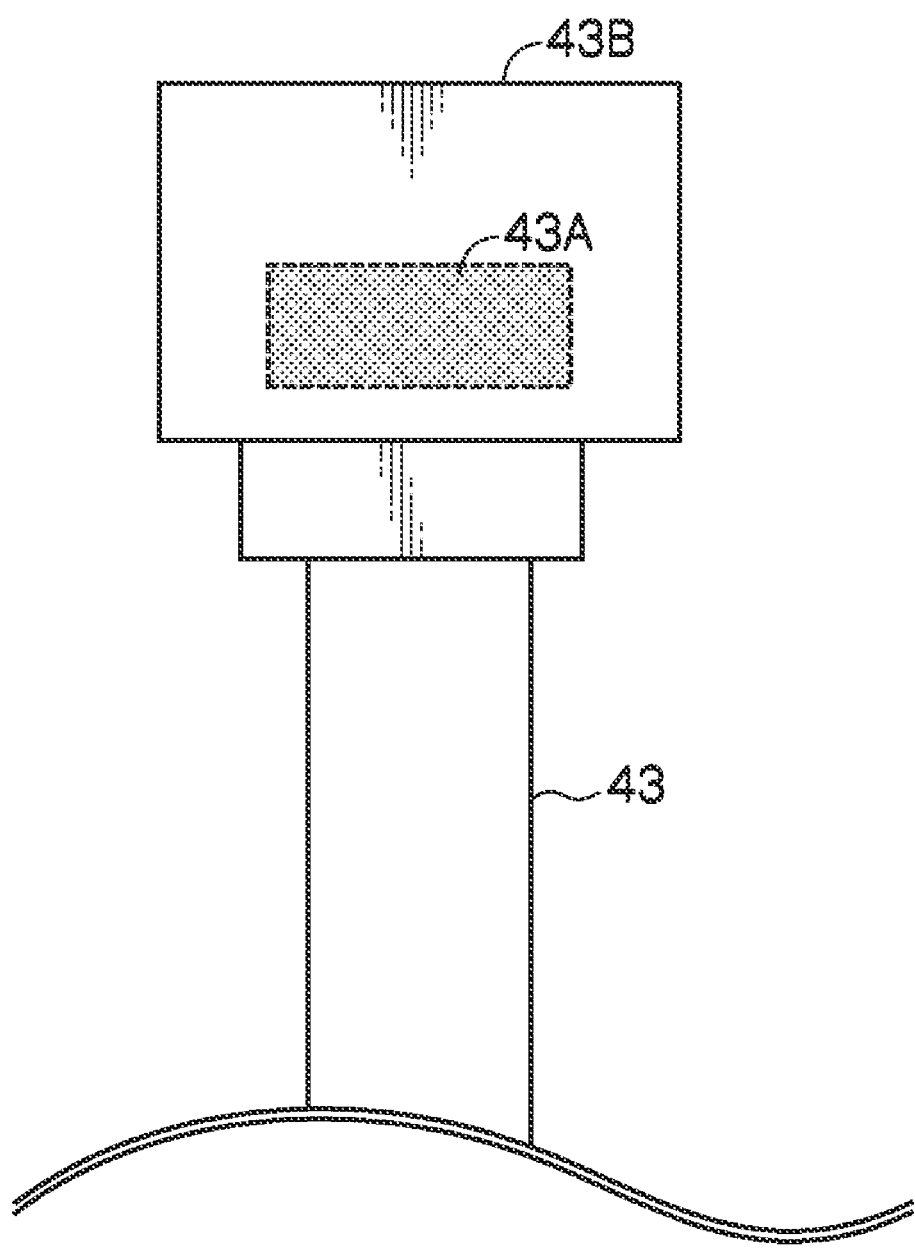
FIG. 19 is a diagram showing a region of the communication cable pertaining to another exemplary embodiment in which a memory is embedded.
Figure 20:
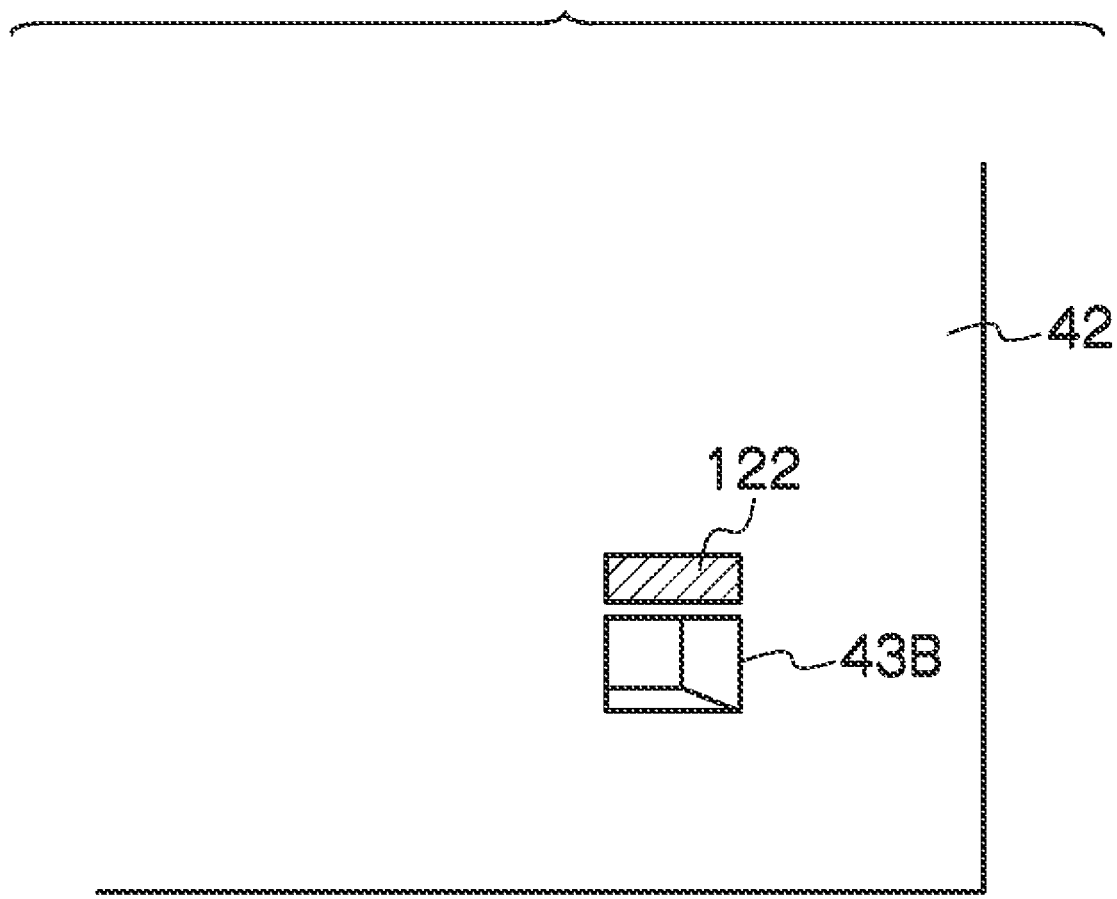
FIG. 20 is a diagram showing one example of a configuration where a reading component is disposed in the vicinity of the connection terminal pertaining to another exemplary embodiment.

Further, for example, a chip that is readable by wireless communication such as radio frequency identification (RFID) may be embedded in the terminal 43B of the communication cable 43 as a memory 43A in which identification information for identifying the communication cable 43 is stored. In FIG. 19, there is shown the region of the terminal 43B in which the memory 43A is embedded. Further, a reading component 122 may be disposed in the vicinity of the connection terminal 42B of the console 42. In FIG. 20, there is shown a diagram showing one example of a configuration where the reading component 122 is disposed in the vicinity of the connection terminal 42B. The reading component 122 reads the identification information in the memory 43A added to the communication cable 43 connected to the connection terminal 42B when the communication cable 43 has been connected to the connection terminal 42B.

In this configuration, the console 42 may detect the state of connection between the connection terminal 32A and the communication cable 43 on the basis of the state of reading of the identification information in the memory 43A added to the communication cable 43 by the reading component 122.

Further, for example, as shown in FIG. 13, the invention may also be configured such that the communication cable 43 connected to the connection terminal 32A is held by a holding member 456 disposed in the electronic cassette 32. In this case, a mechanical switch or a sensor may be disposed in the holding member 458, and the mechanical switch or the sensor may detect the state of holding of the communication cable 43 as the state of connection between the connection terminal 32A and the communication cable 43. Moreover, when the communication cable 43 is embedded and held inside a groove disposed in the electronic cassette 32, a mechanical switch or a sensor may be disposed, and the mechanical switch or the sensor may detect the state of holding of the communication cable 43.

Further, in the preceding exemplary embodiment, a case has been described where the console 42 issues a warning to the doctors 26 or a radiologic technologist by displaying a warning on the display 100, but the present invention is not limited to this. For example, the console 42 may also be configured to output audio using an audio playback device such as a speaker or to output a printout. Further, the console 42 may also combine a plurality of display of a warning on the display 100, audio output from a speaker and output of a printout.

Further, in the preceding exemplary embodiment, a case has been described where the console 42 determines whether or not the communication cable 43 is inappropriate for the transmission of image information on the basis of the state information, but the present invention is not limited to this. For example, the invention may also be configured such that the electronic cassette 32 performs the determination. The warning may be performed by the electronic cassette 32 or by the console 42.

In addition, the configuration of the radiology information system 10, the configuration of the image capturing system 18 and the configuration of the electronic cassette 32 that have been described in the preceding exemplary embodiments are only examples. It goes without saying that these configurations are alterable depending on the situation within a range that does not depart from the gist of the present invention.

Further, the flow (see FIG. 6) of operation when capturing a radiographic image that has been described in the preceding exemplary embodiments is also only an example. It goes without saying that the flow of that operation is alterable depending on the situation within a range that does not depart from the gist of the present invention.

Further, the flows (see FIG. 7, FIG. 8, FIG. 15 and FIG. 18) of processing of programs that have been described in the preceding exemplary embodiments are also only examples. It goes without saying that unnecessary steps can be deleted from the flows of processing of those programs, new steps can be added to the flows of processing of those programs, and the processing order can be changed.

What is claimed is:

1. A portable radiographic image conversion device comprising:
   an electronic circuit that generates image information representing a radiographic image corresponding to an amount of radiation with which the electronic circuit has been irradiated from an external unit;
   a connection terminal for connecting a communication cable that is connected to an external device;
   a communication unit that performs communication with the external device via the communication cable;
   a memory for storing the image information;
   a determination unit which, when the image information has been generated by the electronic circuit, determines whether or not a state of connection between the connection terminal and the communication cable is abnormal; and
   a control unit which, when it has been determined by the determination unit that the state of connection is not abnormal, causes the image information that has been generated to be transmitted by the communication unit and, when it has been determined by the determination unit that the state of connection is abnormal, causes the image information that has been generated to be stored in the memory.

2. The portable radiographic image conversion device according to claim 1, further comprising a communication quality detection unit that detects quality of communication via the communication cable, wherein the determination unit determines whether or not the state of connection between the connection terminal and the communication cable is abnormal on the basis of the communication quality that has been detected by the communication quality detection unit.

3. The portable radiographic image conversion device according to claim 1, further comprising a mechanical switch that is installed in a position where the communication cable is disposed when the communication cable and the connection terminal are connected to each other, wherein the determination unit determines whether or not the state of connection between the connection terminal and the communication cable is abnormal on the basis of an ON or OFF state of the mechanical switch.

4. The portable radiographic image conversion device according to claim 1, further comprising a sensor that detects whether or not the communication cable is connected to the connection terminal, wherein the determination unit determines whether or not the state of connection between the connection terminal and the communication cable is abnormal on the basis of the detection result of the sensor.

5. The portable radiographic image conversion device according to claim 1, further comprising a holding member for holding the communication cable connected to the connection terminal and a sensor that detects a state of holding of the communication cable by the holding member, wherein the determination unit determines whether or not the state of connection between the connection terminal and the communication cable is abnormal on the basis of the detection result of the sensor.

6. The portable radiographic image conversion device according to claim 1, wherein the determination unit determines whether or not the state of connection between the connection terminal and the communication cable is abnormal by determining whether or not a predetermined signal has been received by the communication unit.

7. The portable radiographic image conversion device according to claim 1, wherein the memory is configured by a volatile memory or a nonvolatile memory.

8. A computer-readable medium storing a program causing a computer to execute a process for communication control, the process comprising:
   determining, when an electronic circuit that generates image information representing a radiographic image corresponding to an amount of radiation with which the electronic circuit has been irradiated from an external unit has generated the image information, whether or not a state of connection between a connection terminal for connecting a communication cable that is connected to an external device and the communication cable is abnormal; and
   when it has been determined that the state of connection is not abnormal, causing the image information that has been generated to be transmitted by a communication unit that performs communication with the external device via the communication cable, and, when it has been determined that the state of connection is abnormal, causing the image information that has been generated to be stored in a memory for storing the image information.

9. A warning device comprising:
   an acquisition unit which, with respect to a radiographic image capturing device equipped with a connection terminal and a generation unit that generates image information representing a radiographic image expressed by radiation with which the generation unit has been irradiated, and which radiographic image capturing device transmits, via a communication cable connected to the connection terminal, the image information that has been generated, acquires state information representing a state of connection between the connection terminal and the communication cable;
   a determination unit that determines whether or not the communication cable connected to the connection terminal is inappropriate for transmission of the image information on the basis of the state information that has been acquired by the acquisition unit; and
   a control unit that controls a warning unit such that a warning is issued when it has been determined by the determination unit that the communication cable connected to the connection terminal is inappropriate for transmission of the image information.

10. The warning device according to claim 9, wherein the determination unit determines whether or not the communication cable is inappropriate for transmission of the image information by determining whether or not the state of connection represented by the state information satisfies a condition determined beforehand as being inappropriate for the transmission of image information.

11. The warning device according to claim 9, wherein the determination unit performs the determination at a predetermined timing in a preparatory stage of capturing a radiographic image.

12. The warning device according to claim 9, wherein the state information is at least one of
   information representing a physical state of connection between the connection terminal and the communication cable that has been detected by a mechanical switch or a sensor,
   information representing quality of communication when the communication cable has been connected to the connection terminal and data have been transmitted, and
   information representing a state of holding of the communication cable when the communication cable is connected to the connection terminal and the communication cable is held in a holding member disposed in the radiographic image capturing device.

13. A computer-readable medium storing a program causing a computer to execute a process for warning control, the process comprising:
   acquiring, with respect to a radiographic image capturing device equipped with a connection terminal and a generation unit that generates image information representing a radiographic image expressed by radiation with which the generation unit has been irradiated, and which radiographic image capturing device transmits, via a communication cable connected to the connection terminal, the image information that has been generated, state information representing a state of connection between the connection terminal and the communication cable;
   determining whether or not the communication cable connected to the connection terminal is inappropriate for transmission of the image information on the basis of the state information that has been acquired; and
   controlling a warning unit such that a warning is issued when it has been determined that the communication cable connected to the connection terminal is inappropriate for transmission of the image information.

* * * * *